United States Patent [19]

Pate et al.

[11] Patent Number: 5,977,180

[45] Date of Patent: *Nov. 2, 1999

[54] ANANDAMIDE ANALOG COMPOSITIONS AND METHOD OF TREATING INTRAOCULAR HYPERTENSION USING SAME

[76] Inventors: David W. Pate, Postbus 1397, 1000 BJ Amsterdam, Netherlands; Tomi Jarvinen; Kristina Jarvinen, both of Sompatie 3 I 6, 70200 Kuopio, Finland; Arto Urtti, 8 Whittier Ct., Mill Valley, Calif. 94941

[ * ] Notice: This patent is subject to a terminal disclaimer.

[21] Appl. No.: 08/776,268

[22] PCT Filed: Jul. 10, 1995

[86] PCT No.: PCT/US95/08226

§ 371 Date: Jan. 10, 1997

§ 102(e) Date: Jan. 10, 1997

[87] PCT Pub. No.: WO96/01558

PCT Pub. Date: Jan. 25, 1996

Related U.S. Application Data

[63] Continuation of application No. 08/457,442, Jun. 1, 1995, abandoned, which is a continuation-in-part of application No. 08/272,532, Jul. 11, 1994, Pat. No. 5,631,297.

[51] Int. Cl.$^6$ .................................................. A61K 31/16
[52] U.S. Cl. ........................ 514/627; 514/625; 514/628; 514/629; 514/528; 514/912; 514/913; 514/231.2; 514/315
[58] Field of Search ..................................... 514/627, 625, 514/628, 629, 528, 912, 913, 231.2, 315

[56] References Cited

U.S. PATENT DOCUMENTS

| | | | |
|---|---|---|---|
| 3,649,650 | 3/1972 | Razdan et al. | 260/345.3 |
| 4,327,028 | 4/1982 | Kaplan | 260/345.3 |
| 4,474,811 | 10/1984 | Masuda et al. | 424/317 |
| 4,476,140 | 10/1984 | Sears et al. | 424/283 |
| 4,983,586 | 1/1991 | Bodor | 514/58 |
| 5,070,081 | 12/1991 | Majid et al. | 514/58 |
| 5,418,225 | 5/1995 | Javitt et al. | 514/58 |
| 5,631,297 | 5/1997 | Pate et al. | 514/627 |

FOREIGN PATENT DOCUMENTS

| | | | |
|---|---|---|---|
| 0326196 | 8/1989 | European Pat. Off. | A61K 31/575 |
| 0400637 | 12/1990 | European Pat. Off. | A61K 37/02 |
| 0435682 | 7/1991 | European Pat. Off. | A61K 31/557 |
| 0472327 | 2/1992 | European Pat. Off. | A61K 31/535 |
| WO 9412466 | 6/1994 | WIPO | C07C 23/300 |

OTHER PUBLICATIONS

Felder et al, *Proc. Natl. Acad. Sci. USA*, 90:7656–7660 (1993).
International Cannabis Research Society, 1993 Meeting, Abstracts, pp. 1–2, 9, 14, 23, 29 and 42, Scarborough, Ontario, Canada (Jun. 11–12, 1993).
Devane et al, *J. Med. Chem.*, 35:2065–2069 (1992).
Matsuda et al, *Nature*, 346:561–564 (1990).
Cooler et al, *Southern Medical Journal*, 70(8):951–954 (1977).
Hefler et al, *Jama*, 217(10):1392 (1971).
Hanus et al, *J. Med. Chem.*, 36:3032–3034 (1993).
Devane et al, *Science*, 258:1946–1949 (1992).
Mestel, *New Scientist*, pp. 21–21 (Jul. 1993).
Fackelman, *Science News*, 143:88–89 and 94 (1993).
Fride et al, *European Journal of Pharmacology*, 231:313–314 (1993).
Shoyama et al, *J. Nat. Prod.*, 46(5):633–637 (1983).
Physicians Desk Reference for Ophthalmic, 14th Ed., p. 11 (1972).
Munro et al, *Letters to Nature*, 365:61–65 (1993).
Pate et al, *Current Eye Research*, 14:791–797 (1995).
Pate et al, "Topical Application of Ophthalmic Anandamides Decreases Intraocular Pressure In Normotensive Rabbits", Abstract, p. 54, International Cannabis Research Society, Jun. 10, 1995 Symposium on Cannabis and Cannabinoids.
Jarho et al, *Pharmacology and Toxicology*, 76(Sup II):Abstract (May 18–20, 1995).
Urtti et al, *Investigative Ophthalmology and Visual Science*, Annual Meeting, Fort Lauderdale, Florida (May 14–19, 1995).
Abadji et al, *J. Med. Chem.*, 37:1889–1893 (1994).
Adams et al, *Life Sciences*, 56(23/24):2041–2048 (1995).
Podos et al, *Prostaglandins*, 3(1):7–16 (1973).
Deutsch et al, *Biochemical Pharmacology*, 46(5):791–796 (1993).
Mechoulam et al, "An Endogenous Cannabinoid Ligand Present in Canine Gut that Binds to the Peripheral Cannabinoid Receptor", Abstract, p. 34, International Cannabis Research Society, L'Esterel, Quebec, Canada (Jul. 21–23, 1994).
Pinto et al, *Molecular Pharmacology*, 46:516–522 (1994).

*Primary Examiner*—Samuel Barts
*Assistant Examiner*—Rosalynd Keys
*Attorney, Agent, or Firm*—Sughrue, Mion, Zinn, Macpeak & Seas, PLLC

[57] ABSTRACT

Anandamide analogues useful for the treatment of intraocular hypertension, as well as ophthalmic compositions comprising the same and a cyclodextrin, and methods of use of these compounds to treat intraocular hypertension.

41 Claims, 19 Drawing Sheets

ANANDAMIDE ANALOG COMPOSITIONS AND METHOD OF TREATING INTRAOCULAR HYPERTENSION USING SAME

This application is a 371 of PCT/US95/08226, filed Jul. 10, 1995, which is a continuation of application Ser. No. 08/457442, filed Jun. 1, 1995, now abandoned, which is a CIP of application Ser. No. 08/272,532, filed Jul. 11, 1994, U.S. Pat. No. 5,631,297.

FIELD OF THE INVENTION

The present invention relates to anandamide analogues useful for the treatment of intraocular hypertension, as well as ophthalmic compositions comprising the same and a cyclodextrin, and methods of use of said compositions to treat intraocular hypertension.

BACKGROUND OF THE INVENTION

Subjects who smoke marijuana have reduced intraocular pressure (Helper et al, *J. Am. Med. Assoc.*, 217:1392 (1971)). The primary psychoactive ingredient in marijuana is known to be delta-9-tetrahydrocannabinol ("THC"). Human experiments involving intravenous administration of pure THC have confirmed the intraocular pressure reduction phenomenon seen with subjects who smoke marijuana (Cooler et al, *South. Med. J.*, 70:954 (1977)). As a result, cannabinoids have been investigated as anti-glaucoma agents.

However, use of systemic cannabinoids, such as THC, as anti-glaucoma agents is disadvantageous since they can cause significant adverse psychological and physiological side-effects. In addition, cannabinoids are lipophilic compounds that are very insoluble in water, thus hindering their application as topical ophthalmic pharmaceutical products.

Anandamides are structurally different from cannabinoids, such as THC. The first anandamide discovered (Devane et al, *Science*, 258:1946 (1992)) is represented by the following formula, and is known as arachidonyl ethanolamide:

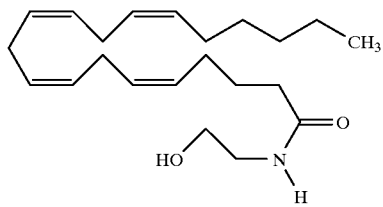

Two other endogenous anandamides were subsequently discovered (Hanus et al, *J. Med. Chem.*, 36:3032 (1993)). Several synthetic analogues have also been made (Felder et al, *Proc. Natl. Acad. Sci. USA*, 90:7656 (1993); Abadji et al, *J. Med. Chem.*, 37: 1889 (1994); Pinto et al, *Pharm. Exp. Therap.*, 46:516 (1994); and Adams et al, *Life Sciences*, 56:2041 (1995)).

Arachidonyl ethanolamide is an endogenous porcine ligand reported to bind to the cannabinoid receptor in the brain (Devane et al, supra). Like THC, anandamides are useful in reducing intraocular pressure (PCT Patent Publication Wo 94/12466). However, it has been discovered in the present invention that many anandamides, when used as a hypotensive agent, have a disadvantage in that a hypertensive effect is induced during the initial phase of action.

Aqueous eyedrops are the most commonly used dosage form for ophthalmic drug delivery. This is because eyedrops are easy to use, relatively inexpensive and do not impair vision. However, the aqueous solubility of anandamides is very poor. Thus, ophthalmic delivery of anandamides in aqueous eyedrops is difficult.

Anandamides are soluble in oil solutions (e.g., castor oil, sesame oil, mineral oil, etc.) and organic solvents (e.g., ethanol, chloroform, etc.). However, these solvents cause harmful side-effects when administered to the eyes. Thus, they are generally not used for ophthalmic drug delivery.

Cyclodextrins ("CDs") are a group of homologous cyclic oligosaccharides consisting of six, seven or eight glucopyranose units, and are respectively called α-, β- or γ-cyclodextrin. It is generally known that CDs can form inclusion complexes with various hydrophobic organic or inorganic compounds, and as a result, increase the solubility or stability of these compounds (Bekers et al, *Drug Dev. Ind. Pharm.*, 17:1503–1549 (1991); and Duchene et al, *Drug Dev. Ind. Pharm.*, 16:2487–2499 (1990)). CDs have also been used to increase the dissolution rate, as well as the bioavailability of various drugs, and to decrease the toxicity of topically applied drugs (Bekers et al, *Drug Dev. Ind. Pharm.*, 17:1503–1549 (1991)).

CDs can be regarded as cone-shaped molecules, where the polar hydroxyl groups of the glucose unit are oriented towards the outside of the structure (Bekers et al, *Drug Dev. Ind. Pharm.*, 17:1503–1549 (1991)). Therefore, the outside of CDs is hydrophilic, whereas the inside of the cavity is hydrophobic in character. The minimum requirement for inclusion complex formation is that the guest molecule must fit, entirely or at least partially, into the CD cavity (Bekers et al, *Drug Dev. Ind. Pharm.*, 17:1503–1549 (1991)).

However, little attention had been paid to the suitability of CDs for use with drugs having ophthalmic activity or for use in ophthalmic compositions. Co-administered CD has increased the ocular absorption of dexamethasone (Loftsson et al, *Int. J. Pharm.*, 104:181–184 (1994), dexamethasone acetate (Usayapant et al, *Pharm. Res.*, 8:1495–1499 (1991) and pilocarpine (Freedman et al, *Curr. Eve Res.*, 12:641–647 (1993), and the intraocular pressure lowering effect of carbonic anhydrase inhibitors (Loftsson et al, *Eur. J. Pharm. Sci.*, 1:175–180 (1994) (see also EP 326196B1, EP 400637A3, EP 435682A2 and EP 472327A1).

SUMMARY OF THE INVENTION

Accordingly, an object of the present invention is to provide compounds useful for the treatment of elevated intraocular pressure (IOP).

An additional object of the present invention is to provide compounds that possess little or no initial hypertensive effect when used for the treatment of elevated IOP.

Another object of the present invention is to provide an ophthalmic composition useful for the reduction of IOP which is delivered non-systemically to the site of action, thereby enhancing the effect on IOP and minimizing entry into the central nervous system.

A further object of the present invention is to provide a method for reducing IOP using said compounds.

These and other objects of the present invention, which will be apparent from the detailed description of the invention provided hereinafter, have been met, in a one embodiment, by anandamides represented by Formula (I) or Formula (II):

Formula (I):

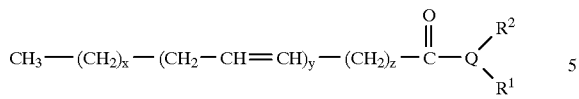

wherein

Q is N;

R¹ and R² are each H, an alkyl having from 1 to 3 carbon atoms or $(CH_2)_a$—R³, wherein a is an integer of from 0 to 6, preferably 1 to 4, more preferably 2 to 3, preferably one of R¹ and R² is H or an alkyl having from 1 to 3 carbon atoms and the other of R and R² is $(CH_2)_a$—R³;

R³ is:
(1) C≡N or SH, preferably C≡N;
(2) a carbocyclic ring having from 3 to 7 carbon atoms, preferably phenyl, or a heterocyclic ring having from 3 to 7 atoms, at least one of which is a heteroatom selected from the group consisting of N, O and S, preferably pyridino or morpholino;
(3) R⁴NR⁵, wherein R⁴ and R⁵ are each H or $(CH_2)_n$—CR⁶R⁷R⁸, wherein n is an integer of from 0 to 3, preferably 0 to 1, and R⁶, R⁷ and R⁸ are each H or $(CH_2)_p$—CH₃, wherein p is an integer of from 0 to 3, preferably 0 to 1; or
(4)

$$NH-\overset{O}{\underset{\|}{C}}-R^9,$$

wherein R⁹ is H or $(CH_2)_q$—CR¹⁰R¹¹R¹², wherein q is an integer of from 0 to 3, preferably from 0 to 1, and R¹⁰, R¹¹ and R¹² are each H or $(CH_2)_r$—CH₃, wherein r is an integer of from 0 to 3;

R¹ and R² may be combined together with Q to form a heterocyclic ring having 3 to 7 atoms, wherein the heterocyclic ring may have an additional heteroatom(s) selected from the group consisting of N, O and S, preferably morpholino;

x is an integer of from 0 to 18, preferably 2 to 5;
y is an integer of from 0 to 8, preferably 2 to 4; and
z is an integer of from 0 to 18, preferably 2 to 5;
wherein x+y+z≦36, preferably ≦24, more preferably ≦18, most preferably ≦12.

Formula (II):

Q is N;

R¹' and R²' are each H, an alkyl having from 1 to 3 carbon atoms or $(R^{4'}CR^{5'})$—$(CH_2)_{a'}$—R³', wherein a' is an integer of from 0 to 5, preferably 0 to 3, more preferably 1 to 2, preferably one of R¹' and R²' is H or an alkyl having from 1 to 3 carbon atoms and the other of R¹' and R²' is $(R^{4'}CR^{5'})$—$(CH_2)_{a'}$—R³';

R³' is:
(1) OH, SH, C≡CH, C≡N, F, Cl, Br or I, preferably SH, more preferably F; even more preferably C≡CH, most preferably C≡N;

(2) a carbocyclic ring having from 3 to 7 carbon atoms, preferably phenyl, or a heterocyclic ring having from 3 to 7 atoms, at least one of which is a heteroatom selected from the group consisting of N, O and S, preferably pyridino or morpholino;
(3) R⁴NR⁵, wherein R⁴ and R⁵ are each H or $(CH_2)_n$—CR⁶R⁷R⁸, wherein n is an integer of from 0 to 3, preferably 0 to 1, and R⁶, R⁷ and R⁸ are each H or $(CH_2)_p$—CH₃, wherein p is an integer of from 0 to 3, preferably 0 to 1;
(4)

$$NH-\overset{O}{\underset{\|}{C}}-R^9,$$

wherein R⁹ is H or $(CH_2)_q$—CR¹⁰R¹¹R¹², wherein q is an integer of from 0 to 3, preferably from 0 to 1, and R¹⁰, R¹¹ and R¹² are each H or $(CH_2)_r$—CH₃, wherein r is an integer of from 0 to 3; or
(5) OCR¹³R¹⁴R¹⁵, wherein R¹³, R¹⁴, R¹⁵ are each H or $(CH_2)_s$—CH₃, wherein s is an integer of from 0 to 3, preferably 0 to 1;

R⁴' and R⁵' are each H, $(CH_2)_l$—R³', wherein R³' is a carbocyclic ring having from 3 to 7 carbon atoms or a heterocyclic ring having from 3 to 7 atoms, at least one of which is a heteroatom selected from the group consisting of N, O and S, or $(CH_2)_l$—CR⁶'R⁷'R⁸', wherein l is an integer of from 0 to 3, preferably 1, more preferably 0, and R⁶', R⁷', and R⁸' are each H or $(CH_2)_m$—CH₃, wherein m is an integer of from 0 to 3, preferably 0, preferably only one of R⁴' and R⁵' is H;

R¹' and R²' may be combined together with Q to form a heterocyclic ring having 3 to 7 atoms, wherein the heterocyclic ring may have an additional heteroatom(s) selected from the group consisting of N, O and S, preferably morpholino;

R⁴' and R⁵' may be combined together to form a carbocyclic ring having from 3 to 7 carbon atoms, or may be combined with a heteroatom(s) selected from the group consisting of N, O and S to form a heterocyclic ring having from 3 to 7 atoms;

R⁴ or R⁵ may be combined together with Q to form a heterocyclic ring having from 3 to 7 atoms, wherein the heterocyclic ring may have an additional heteroatom(s) selected from the group consisting of N, O and S;

x is an integer of from 0 to 18, preferably 2 to 5;
y is an integer of from 0 to 8, preferably 2 to 4; and
z is an integer of from 0 to 18, preferably 2 to 5;
wherein x+y+z≦36, preferably ≦24, more preferably ≦18, most preferably ≦12.

In another embodiment, the above-described objects have been met by an ophthalmic composition for reducing intraocular pressure comprising an admixture of a pharmaceutically effective amount of a compound represented by Formula (I) or Formula (II), and a cyclodextrin.

In still another embodiment, the above-described objects have been met by a method for treatment of intraocular hypertension comprising topically administering a pharmaceutically effective amount of a compound represented by Formula (I) or Formula (II) to an affected eye in need of such treatment.

DETAILED DESCRIPTION OF THE INVENTION

Figure 1A:
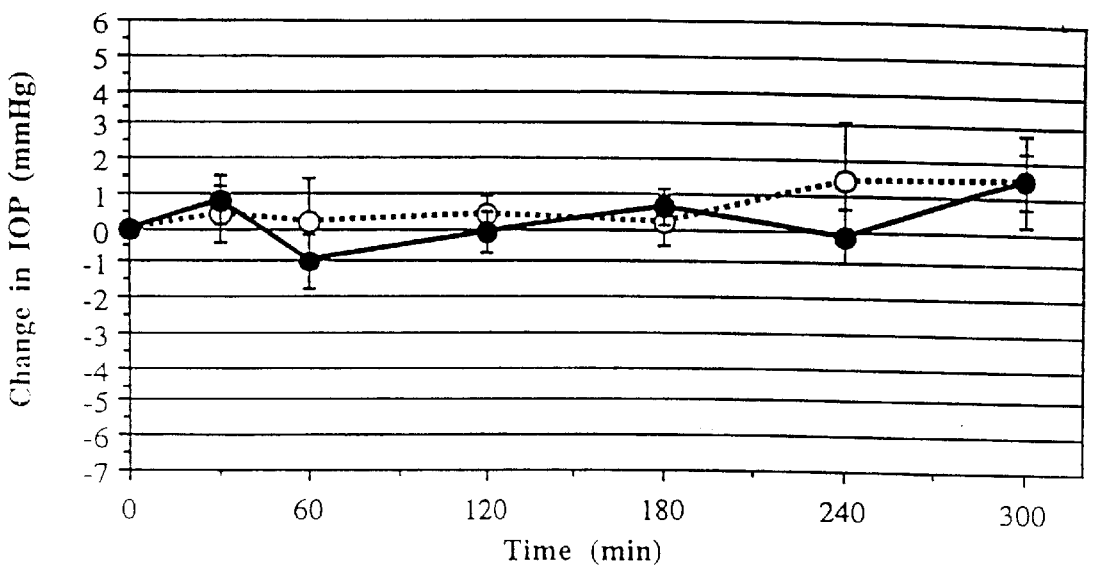
FIG. 1A shows the IOP changes in normotensive pigmented rabbits (treated eyes) after unilateral ocular administration (25 μl) of 5.0% (w/v) 2-OH-propyl-β-cyclodextrin (○) or 0.9% (w/v) NaCl (•), mean±S.E. (n=5).

As discussed above, anandamides of the present invention are represented by Formula (I) or Formula (II):

Formula (I):

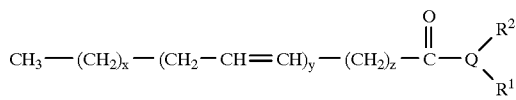

wherein

Q is N;

$R^1$ and $R^2$ are each H, an alkyl having from 1 to 3 carbon atoms or $(CH_2)_a$—$R^3$, wherein a is an integer of from 0 to 6, preferably 1 to 4, more preferably 2 to 3, preferably one of $R^1$ and $R^2$ is H or an alkyl having from 1 to 3 carbon atoms, and the other of $R^1$ and $R^2$ is $(CH_2)_a$—$R^3$;

$R^3$ is:

(1) C≡N or SH, preferably C≡N;

(2) a carbocyclic ring having from 3 to 7 carbon atoms, preferably phenyl, or a heterocyclic ring having from 3 to 7 atoms, at least one of which is a heteroatom selected from the group consisting of N, O and S, preferably pyridino or morpholino;

(3) $R^4NR^5$, wherein $R^4$ and $R^5$ are each H or $(CH_2)_n$—$CR^6R^7R^8$, wherein n is an integer of from 0 to 3, preferably 0 to 1, and $R^6$, $R^7$ and $R^8$ are each H or $(CH_2)_p$—$CH_3$, wherein p is an integer of from 0 to 3, preferably 0 to 1; or (4)

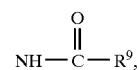

wherein $R^9$ is H or $(CH_2)_q$—$CR^{10}R^{11}R^{12}$, wherein q is an integer of from 0 to 3, preferably from 0 to 1, and $R^{10}$, $R^{11}$ and $R^{12}$ are each H or $(CH_2)_r$—$CH_3$, wherein r is an integer of from 0 to 3;

$R^1$ and $R^2$ may be combined together with Q to form a heterocyclic ring having 3 to 7 atoms, wherein the heterocyclic ring may have an additional heteroatom(s) selected from the group consisting of N, O and S, preferably morpholino;

x is an integer of from 0 to 18, preferably 2 to 5;

y is an integer of from 0 to 8, preferably 2 to 4; and z is an integer of from 0 to 18, preferably 2 to 5;

wherein x+y+z≦36, preferably≦24, more preferably≦18, most preferably≦12.

Specific non-limiting examples of the compounds represented by Formula (I) which can be employed in the present invention include the following:

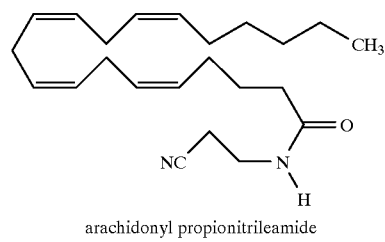

arachidonyl propionitrileamide

Formula (I):
$R^1$=$(CH_2)_a$—$R^3$; $R^2$=H; $R^3$=CN;
a=2; x=3; y=4; and z=3.

Another example of a compound within the scope of Formula (I) which can be employed in the present invention is arachidonyl ethanethiolamide.

Further specific non-limiting examples of the compounds represented by Formula (I) which can be employed in the present invention include arachidonyl β-phenethylamide, arachidonyl N-acetylaminoethylamide, arachidonyl N,N-dimethylaminoethylamide, arachidonyl aminoethylamide, arachidonyl pyridinoethylamide and arachidonyl morpholineamide.

As discussed above, the anandamide analogues of the present invention are also represented by Formula (II):

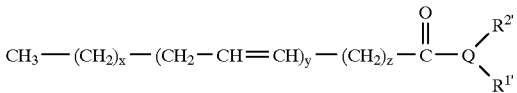

wherein

Q is N;

$R^{1'}$ and $R^{2'}$ are each H, an alkyl having from 1 to 3 carbon atoms or $(R^{4'}CR^{5'})$—$(CH_2)_{a'}$—$R^{3'}$, wherein a' is an integer of from 0 to 5, preferably 0 to 3, preferably 1 to 2, preferably one of $R^{1'}$ and $R^{2'}$ is H or an alkyl having from 1 to 3 carbon atoms and the other of $R^{1'}$ and $R^{2'}$ is $(R^{4'}CR^{5'})$—$(CH_2)_{a'}$—$R^{3'}$;

$R^{3'}$ is:

(1) OH, SH, C≡CH, C≡N, F, Cl, Br or I, preferably SH, more preferably F; even more preferably C≡CH, most preferably C≡N;

(2) a carbocyclic ring having from 3 to 7 carbon atoms, preferably phenyl, or a heterocyclic ring having from 3 to 7 atoms, at least one of which is a heteroatom selected from the group consisting of N, O and S, preferably pyridino or morpholino;

(3) $R^4NR^5$, wherein $R^4$ and $R^5$ are each H or $(CH_2)_n$—$CR^6R^7R^8$, wherein n is an integer of from 0 to 3, preferably 0 to 1, and $R^6$, $R^7$ and $R^8$ are each H or $(CH_2)_p$—$CH_3$, wherein p is an integer of from 0 to 3, preferably 0 to 1;

(4)

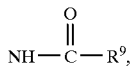

wherein $R^9$ is H or $(CH_2)_q$—$CR^{10}R^{11}R^{12}$, wherein q is an integer of from 0 to 3, preferably from 0 to 1, and $R^{10}$, $R^{11}$ and $R^{12}$ are each H or $(CH_2)_r$—$CH_3$, wherein r is an integer of from 0 to 3; or (5) $OCR^{13}R^{14}R^{15}$, wherein $R^{13}$, $R^{14}$, $R^{15}$ are each H or $(CH_2)_s$—$CH_3$, wherein s is an integer of from 0 to 3, preferably 0 to 1;

$R^{4'}$ and $R^{5'}$ are each H, $(CH_2)_t$—$R^{3'}$, where $R^{3'}$ is a carbocyclic ring having from 3 to 7 carbon atoms, or a heterocyclic ring having from 3 to 7 atoms, at least one of which is a heteroatom selected from the group consisting of N, O and S, or $(CH_2)_l$—$CR^{6'}R^{7'}R^{8'}$, wherein l is an integer of from 0 to 3, preferably 1, more preferably 0, and $R^{6'}$, $R^{7'}$, and $R^{8'}$ are each H or $(CH_2)_m$—$CH_3$, wherein m is an integer of from 0 to 3, preferably from 0 to 1, preferably only one of $R^{4'}$ and $R^{5'}$ is H;

$R^{1'}$ and $R^{2'}$ may be combined together with Q to form a heterocyclic ring having 3 to 7 atoms, wherein the heterocyclic ring may have an additional heteroatom(s) selected from the group consisting of N, O and S, preferably morpholino;

$R^{4'}$ and $R^{5'}$ may be combined together to form a carbocyclic ring having from 3 to 7 carbon atoms, or may be combined with a heteroatom(s) selected from the group consisting of N, O and S to form a heterocyclic ring having from 3 to 7 atoms;

$R^4$ or $R^5$ may be combined together with Q to form a heterocyclic ring having from 3 to 7 atoms, wherein the heterocyclic ring may have an additional heteroatom(s) selected from the group consisting of N, O and S;

x is an integer of from 0 to 18, preferably 2 to 5;

y is an integer of from 0 to 8, preferably 2 to 4; and z is an integer of from 0 to 18, preferably 2 to 5;

wherein $x+y+z \leq 36$, preferably $\leq 24$, more preferably $\leq 18$, most preferably $\leq 12$.

Specific non-limiting examples of the compounds represented by Formula (II) which can be employed in the present invention include the following:

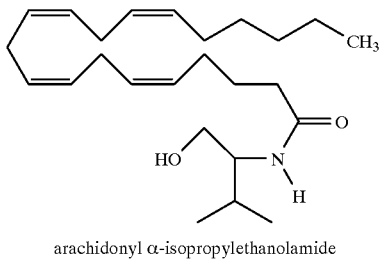

arachidonyl α-isopropylethanolamide

Another example of a compound within the scope of Formula (II) which can be employed in the present invention is arachidonyl α-methylethanolamide, which is described by Felder et al, supra, and is a compound of Formula (I), wherein $R^{1'}=(R^{4'}CR^{5'})$—$(CH_2)_{a'}$—$R^{3'}$; $R^{2'}=H$; $R^{3'}=OH$;
$R^{4'}=(CH_2)_l$—$CR^{6'}, R^{7'}$, $R^{8'}$; $R^{5'}=H$; $R^{6'}=H$; $R^{7'}=H$;
$R^{8'}=H$; a'=1; l=0; x=3; y=4; and z=3.

Further specific non-limiting examples of the compounds represented by Formula (II) which can be employed in the present invention include arachidonyl α-dimethylethanolamide, arachidonyl α-phenylethanolamide, arachidonyl α-isobutylethanolamide, and arachidonyl α-tertbutylethanolamide.

All of the compounds within Formula (I) and Formula (II) can be synthesized according to the methods of Devane et al, *Science*, 258:1946 (1992), by utilizing the appropriate fatty acid chloride and amine. In addition, some precursors may be protected/deprotected before/after the formative reaction, by methods well-known in the art (Greene et al, *Protective Groups in Organic Synthesis*, 2nd Ed., Wiley Interscience, pages 10–143 (1991)).

In the present invention, the insolubility of the compounds represented by Formula (I) or Formula (II) in aqueous solutions has been overcome by the admixture thereof with CDs which do not cause harmful ocular side-effects in patients.

Due to their hydrophilic character and size, CDs are not transported through the cell membranes (Frijlink et al, *Int. J. Pharm.*, 64:195–205 (1990); and Nakanishi et al, *Chem. Pharm. Bull.*, 37:1395–1398 (1989)). In addition, CDs have low general toxicity, and only small amounts are necessary to administer in topical ophthalmic compositions (Doorne, *Eur. J. Pharm. Biopharm.*, 39:133–139 (1993)). For these reasons, little or no side-effects are observed after topical intraocular administration. Thus, CDs demonstrate great utility as useful adjuvants in the ophthalmic compositions of the present invention.

Examples of the cyclodextrin which can be employed in the ophthalmic compositions of the present invention include α-cyclodextrins, β-cyclodextrins and γ-cyclodextrins, and derivatives thereof, such as cyclodextrin ethers (alkyl, e.g., methyl and ethyl, ethers or hydroxyalkyl, e.g., hydroxyethyl and hydroxypropyl, ethers) and esters (acylates, sulfonates, sulfates and phosphates). For ease of formulation (inclusion efficiency), economical reasons and commercial availability, the cyclodextrin is preferably a β-cyclodextrin, more preferably a β-cyclodextrin alkylated or hydroxyalkylated in the 2-, 3- and/or 6-position. Particularly useful β-cyclodextrins include 2-hydroxypropyl-β-cyclodextrin and heptakis-(2,6-di-O-methyl)-β-cyclodextrin.

The amount of compound represented by Formula (I) or Formula (II) to be employed in the ophthalmic compositions of the present invention is generally about 0.01 to 2.0% (w/v), preferably about 0.1% to 0.5% (w/v).

The amount of cyclodextrin to be employed in the ophthalmic compositions of the present invention is generally about 0.5 to 40% (w/v), preferably about 5.0% to 25% (w/v).

The ophthalmic compositions of the present invention are prepared by adding a cyclodextrin to an aqueous solution comprising the compound represented by Formula (I) or Formula (II) so as to form an inclusion complex with the cyclodextrin. As a result, the aqueous solubility of the compound can be increased to a level sufficient for topical intraocular administration, which is undoubtedly desirable for long-term therapy of intraocular hypertension.

In the present invention, the compounds represented by Formula (I) and Formula (II) are topically delivered non-systemically to the site of action, enhancing the effect, and minimizing entry into the central nervous system.

According to the present invention, after topical administration of, e.g., eyedrops, containing a compound represented by Formula (I) and Formula (II), and a cyclodextrin, the compound is first released from the inclusion complex on the precorneal area where it is then able to penetrate across the cornea to reach the inner eye and the site of action.

It is commonly known that ophthalmic drugs decrease IOP less in normotensive rabbits than in hypertensive (glaucoma) rabbits (Vartiainen et al, *Invest. Ophthalmol. Vis. Sci.*, 33:2019–2023 (1992); and Muchtar et al, *Ophthalmic. Res.*, 24:142–149 (1992)). Generally, the rabbit is the most commonly used animal model in ocular drug research because its eye size is similar to humans, and because rabbits are relatively small and easy to handle (Greaves et al, *STP Pharm. Sci.*, 2:13–33 (1992)).

It was found in the present invention that topical administration of 2-hydroxypropyl-β-cyclodextrin or heptakis-(2, 6-di-O-methyl)-β-cyclodextrin in combination with the compounds represented by Formula (I) and Formula (II) are particularly effective in decreasing IOP in treated eyes of normotensive rabbits.

One aspect of the present invention is based on the discovery that unilateral application of the compounds represented by Formula (I) and Formula (II) decreases the IOP in treated eyes, but does not significantly induce an initial hypertensive effect in normotensive rabbits. Thus, it has been found for the first time in the present invention that these compounds act locally within the eye to lower intraocular pressure without a significant initial hypertensive phase, perhaps via avoidance of spasm to the ciliary muscle surrounding the duct through which the eye fluids drain, and result in the reduction of intraocular pressure.

The ophthalmic compositions of the present invention may also include water-soluble polymeric compounds for use as a viscosity enhancing agent. Examples of such water-soluble polymeric compounds include hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid and polyacrylic acid.

The viscosity enhancing agents may be used in the ophthalmic compositions of the present invention in amounts which result in a viscosity in the range of about 1 to 1,000 cP, preferably about 5 to 50 cP.

The ophthalmic compositions of the present invention may further comprise a buffering agent, such as acetate, citrate, phosphate and borate buffers, or mixtures of these buffers.

The concentration of the buffering agent which may be used in the ophthalmic compositions of the present invention is in the range of about 1.0 mM to 200 mM, preferably about 10 mM to 100 mM.

The pH of the ophthalmic composition of the present invention should be in the range of about 4.0 to 8.0, and more specifically about 6.0 to 7.4.

The ophthalmic compositions of the present invention may also include additional carrier adjuvants, including conventional additives, such as a preservative (e.g., benzalkonium chloride, benzyl alcohol, chlorbutanol, chlorhexidine, etc.) or an antioxidant (e.g., sodium bisulfite, sodium thiosulfite, EDTA, etc.). The concentration of these additives in the composition will be selected according to their type/concentration.

The pharmaceutically effective amount of the compound represented by Formula (I) and Formula (II) to be topically administered to the effected eye will generally vary depending upon the age, weight, sex and severity of hypertension in the eye. Typically, the pharmaceutically effective amount will be in the range of about 0.05 to 30 μg/kg body weight, preferably about 0.5 to 10 μg/kg body weight.

The following examples are provided for illustrative purposes only, and are in no way intended to limit the scope of the present invention.

Comparative Examples 1 to 3 below demonstrate that varying concentrations of cyclodextrins, by themselves, do not act to reduce IOP.

COMPARATIVE EXAMPLE 1

In this example, the effect of a 5.0% (w/v) 2-OH-propyl-β-cyclodextrin solution on intraocular pressure (IOP) of normotensive pigmented rabbits (weighing between 2.6–3.6 kg; n=5) of both sexes was studied. The rabbits were housed separately in cages under standard laboratory conditions, i.e., 10 hr dark/14 hr light cycle.

More specifically, 250 mg of 2-OH-propyl-β-CD was added to 5.0 ml of distilled water, and the solution was adjusted to pH 7.0 with sodium hydroxide/hydrochloric acid. Then, distilled water was added to adjust the total volume to 5.0 ml. The osmolality of the solution was adjusted to isotonic, 301 mOsm/kg, with sodium chloride.

As a control, a 0.9% (w/v) NaCl was also prepared.

Then, 25 μl of the 5.0% (w/v) CD solution or the NaCl solution was administered unilaterally. Again, the rabbits were kept in restraint boxes during the study and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before CD or 0.9% (w/v) NaCl solution administration, and were continued 5 hr after administration.

The IOPs of the pigmented rabbits at the time of eyedrop administration were between 15.2–21.9 mmHg (n=5).

Figure 1B:
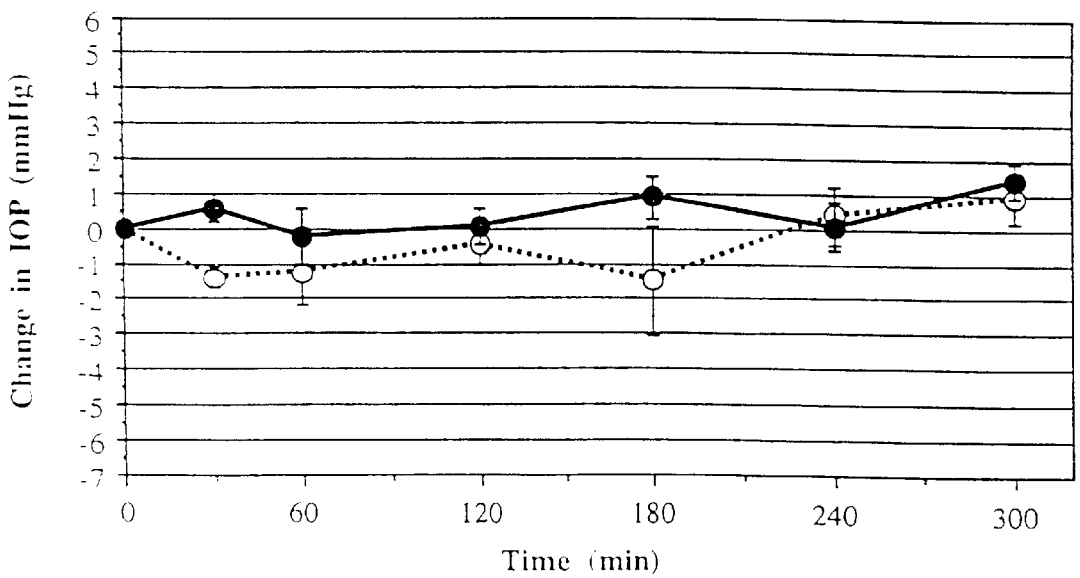
FIG. 1B shows the IOP changes in normotensive pigmented rabbits (untreated eyes) after unilateral ocular administration (25 μl) of 5.0% (w/v) 2-OH-propyl-β-cyclodextrin (○) or 0.9% (w/v) NaCl (•), mean±S.E. (n=5).

The results are shown in FIGS. 1A and 1B, and Table I below. All of the values are expressed as the mean±standard error of means (X±S.E.).

TABLE I

Intraocular Pressure Changes (mmHg) at Predetermined Times (h) in
Normotensive Pigmented Rabbits After Unilateral Administration of Eyedrops
(mean ± S.E., n = 5–6)

| Solution | 0 h | 0.5 h | 1 h | 2 h | 3 h | 4 h | 5 h |
|---|---|---|---|---|---|---|---|
| Treated eye | | | | | | | |
| 0.9% NaCl | 0 ± 0 | 0.8 ± 0.7 | −1.0 ± 0.8 | −0.1 ± 0.6 | 0.6 ± 0.5 | −0.2 ± 0.8 | 1.5 ± 0.8 |
| 5.0% 2-OH-propyl-β-CD | 0 ± 0 | 0.4 ± 0.8 | 0.2 ± 1.2 | 0.4 ± 0.5 | 0.2 ± 0.7 | 1.4 ± 1.7 | 1.5 ± 1.3 |
| 12.5% 2-OH-propyl-β-CD | 0 ± 0 | 0.0 ± 1.1 | −0.1 ± 1.3 | −0.7 ± 1.1 | 0.2 ± 0.8 | 0.8 ± 0.9 | 2.1 ± 0.9 |
| 0.25% Arachidonyl ethanolamide in 5.0% 2-OH-propyl-β-CD | 0 ± 0 | 2.5 ± 1.3 | −3.4 ± 1.0 | −5.2 ± 1.3 | −2.6 ± 1.6 | −0.9 ± 1.5 | −0.2 ± 1 + 1 |
| Untreated eye (contralateral) | | | | | | | |
| 0.9% NaCl | 0 ± 0 | 0.6 ± 0.4 | −0.2 ± 0.8 | 0.1 ± 0.5 | 0.9 ± 0.6 | 0.1 ± 0.7 | 1.4 ± 0.5 |
| 5.0% 2-OH-propyl-β-CD | 0 ± 0 | −1.4 ± 0.3 | −1.3 ± 0.9 | −0.4 ± 0.6 | −1.5 ± 1.6 | 0.4 ± 0.8 | 0.9 ± 0.7 |
| 12.5% 2-OH-propyl-β-CD | 0 ± 0 | −0.6 ± 1.2 | −1.1 ± 0.7 | −1.4 ± 1.0 | 0.6 ± 1.4 | 0.8 ± 1.2 | 0.5 ± 1.2 |
| 0.25% Arachidonyl ethanolamide in 5.0% 2-OH-propyl-β-CD | 0 ± 0 | −2.1 ± 0.3 | −1.6 ± 1.1 | −0.3 ± 1.7 | −0.3 ± 0.5 | 0.3 ± 1.8 | −0.1 ± 1.5 |

As shown in FIGS. 1A and 1B, and Table I above, the unilateral intraocular administration of a 5.0% (w/v) solution of 2-OH-propyl-β-cyclodextrin alone does not greatly affect the IOP of treated or untreated (contralateral) eyes in normotensive pigmented rabbits when compared to administration of the 0.9% (w/v) NaCl solution.

COMPARATIVE EXAMPLE 2

In this example, the effect of a 12.5% (w/v) 2-OH-propyl-β-cyclodextrin solution on intraocular pressure (IOP) of normotensive pigmented rabbits (weighing between 2.1–3.6 kg; n=6) of both sexes was studied. The rabbits were housed separately in cages under standard laboratory conditions, i.e., 10 hr dark/14 hr light cycle.

More specifically, 1250 mg of 2-OH-propyl-β-CD was added to 10.0 ml of distilled water, and the solution was adjusted to pH 5.0 with sodium hydroxide/hydrochloric acid. Then, distilled water was added to adjust the total volume to 10 ml. The osmolality of the solution was adjusted to isotonic, 300 mOsm/kg, with sodium chloride.

As a control, a 0.9% (w/v) NaCl was also prepared.

Then, 25 μl of the 12.5% (w/v) CD solution or the NaCl solution was administered unilaterally. Again, the rabbits were kept in restraint boxes during the study and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before CD or 0.9% (w/v) NaCl solution administration, and were continued 5 hr after administration.

The IOPs of the pigmented rabbits at the time of eyedrop administration were between 18.9–25.7 mmHg (n=6).

Figure 2A:
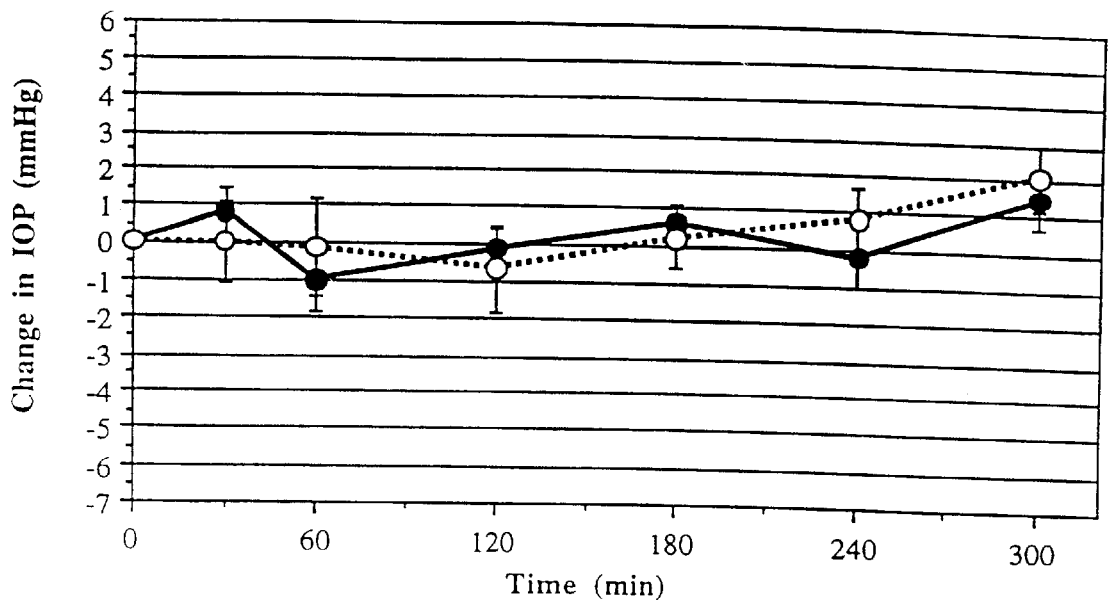
FIG. 2A shows the IOP changes in normotensive pigmented rabbits (treated eyes) after unilateral ocular administration (25 μl) of 12.5% (w/v) 2-OH-propyl-β-cyclodextrin (○) or 0.9% (w/v) NaCl (•), mean±S.E. (n=6).
Figure 2B:
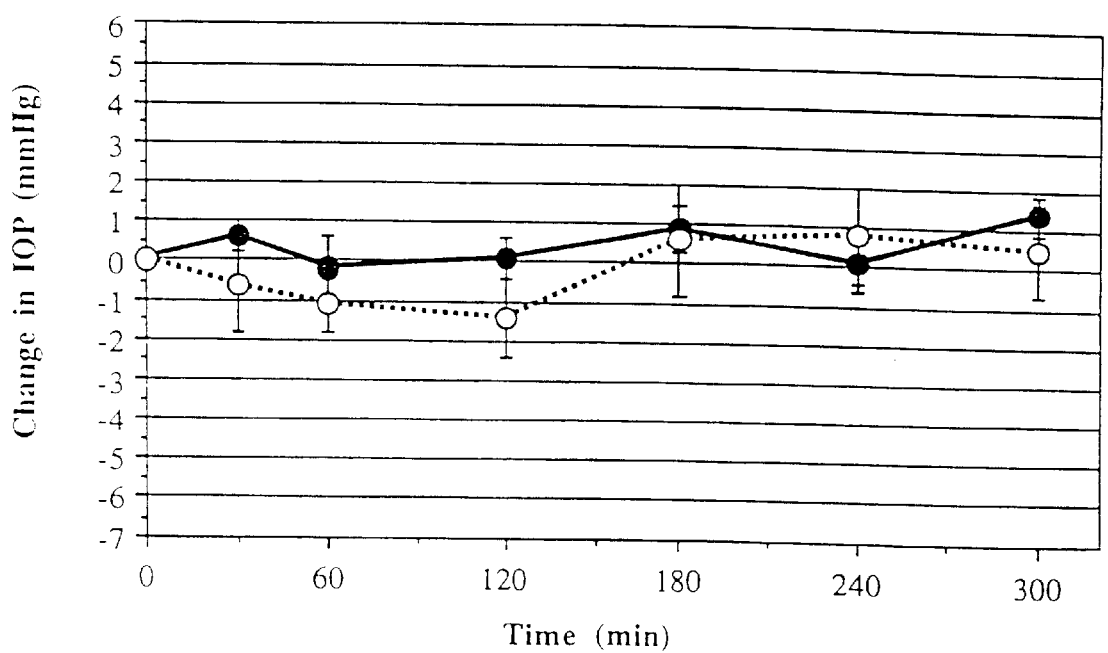
FIG. 2B shows the IOP changes in normotensive pigmented rabbits (untreated eyes) after unilateral ocular administration (25 μl) of 12.5% (w/v) 2-OH-propyl-β-cyclodextrin (○) or 0.9% (w/v) NaCl (•), mean±S.E. (n=6).

The results are shown in FIGS. 2A and 2B, and Table I above. All of the values are expressed as the mean±standard error of means (X±S.E.).

As shown in FIGS. 2A and 2B, and Table I above, the unilateral intraocular administration of a 12.5% (w/v) solution of 2-OH-propyl-β-cyclodextrin alone does not greatly affect the IOP of treated or untreated (contralateral) eyes in normotensive pigmented rabbits when compared to administration of the 0.9% (w/v) NaCl solution.

COMPARATIVE EXAMPLE 3

In this example, the effect of a 30% (w/v) 2-OH-propyl-β-cyclodextrin solution on intraocular pressure (IOP) of normotensive albino (New Zealand strain) rabbits (weighing between 3.3–4.3 kg, n=4) of both sexes was studied. The rabbits were housed separately in cages under standard laboratory conditions, i.e., 10 hr dark/14 hr light cycle.

More specifically, 3000 mg of 2-OH-propyl-β-CD were added to 10 ml of distilled water, and the solution was adjusted to pH 7.0 with sodium hydroxide/hydrochloric acid. Then, distilled water was added to adjust the total volume to 10 ml. The osmolality of the solution was adjusted to isotonic, 436 mOsm/kg, with sodium chloride.

As a control, a 0.9% (w/v) NaCl was also prepared.

Then, 25 μl of the 30% (w/v) CD solution or the NaCl solution was administered unilaterally. The rabbits were kept in restraint boxes during the study, and IOP was measured using a BioRad (Cambridge, Mass.) Digilab Modular One Pneumatonometer. Before each measurement, one or two drops of 0.06% (w/v) oxybuprocaine were applied to the cornea before tonometry to eliminate discomfort. For each determination at least two readings were taken from each eye. The measurements were started 2 hr before the CD or 0.9% (w/v) NaCl solution administration, and were continued 5 hr after administration.

The IOPs of the albino rabbits at the time of eyedrop administration were between 12.4–23.8 mmHg (n=4).

Figure 3A:
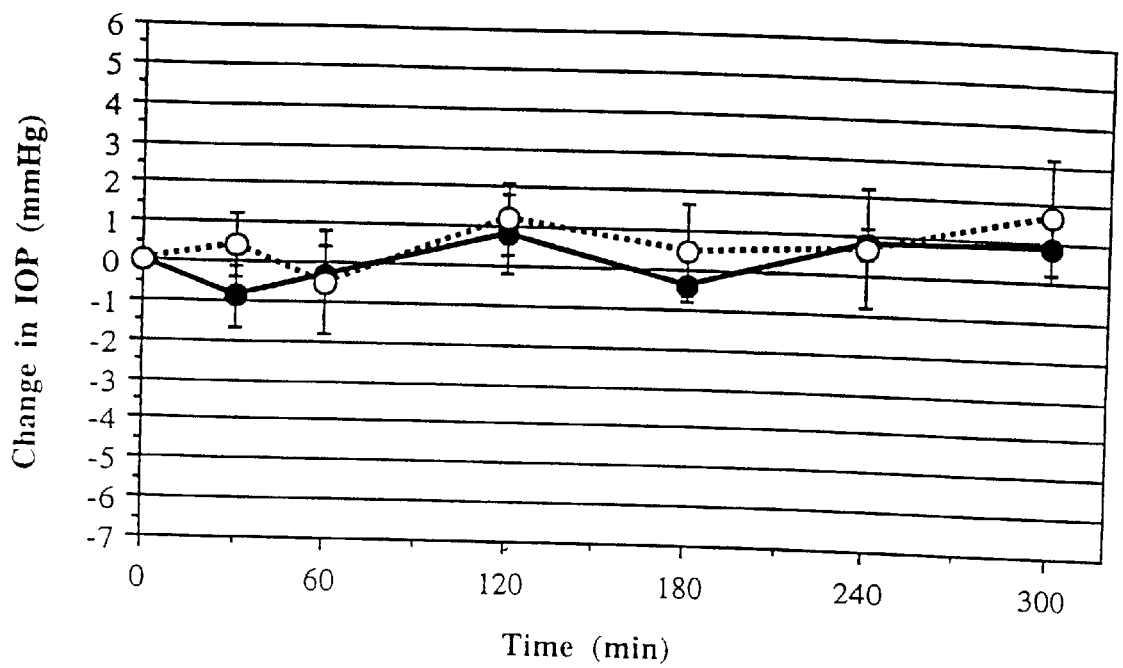
FIG. 3A shows the IOP changes in normotensive albino rabbits (treated eyes) after unilateral ocular administration (25 μl) of 30% (w/v) 2-OH-propyl-β-cyclodextrin (○) or 0.9% (w/v) NaCl (•), mean±S.E. (n=4).
Figure 3B:
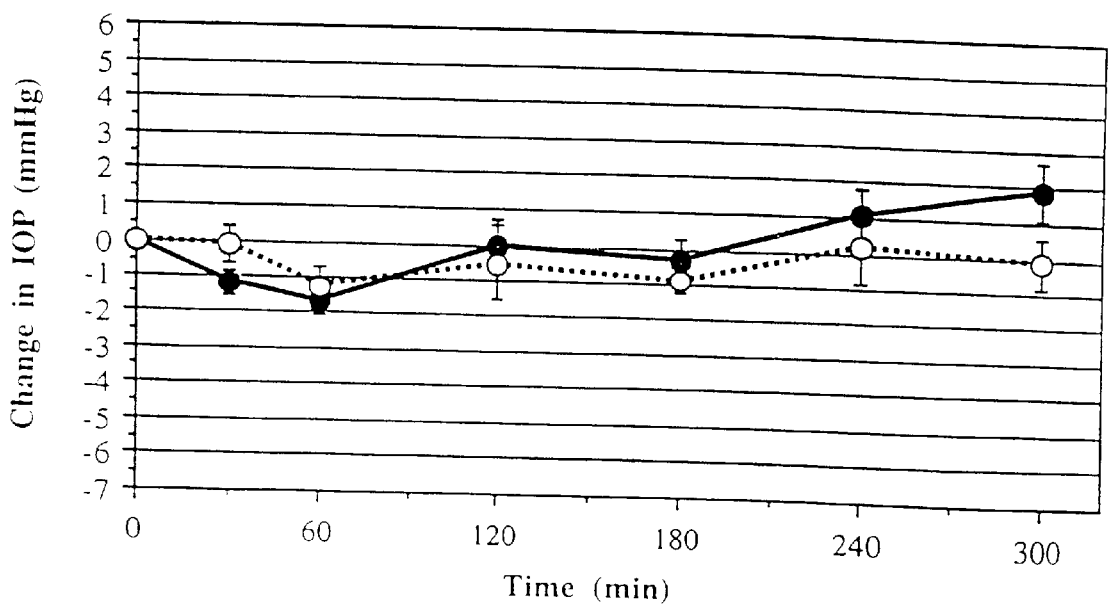
FIG. 3B shows the IOP changes in normotensive albino rabbits (untreated eyes) after unilateral ocular administration (25 μl) of 30% (w/v) 2-OH-propyl-β-cyclodextrin (○) or 0.9% (w/v) NaCl (•), mean±S.E. (n=4).

The results are shown in FIGS. 3A and 3B, and Table II below. All of the values are expressed as the mean±standard error of means (X±S.E.).

TABLE II

Intraocular Pressure Changes (mmHg) at Predetermined Times (h) in
Normotensive Albino Rabbits After Unilateral Administration of Eyedrops
(mean ± S.E., n = 4)

| Solution | 0 h | 0.5 h | 1 h | 2 h | 3 h | 4 h | 5 h |
| --- | --- | --- | --- | --- | --- | --- | --- |
| Treated eye | | | | | | | |
| 0.9% NaCl | 0 ± 0 | −0.9 ± 0.8 | −0.3 ± 0.7 | 0.8 ± 1.0 | −0.4 ± 0.4 | 0.8 ± 0.4 | 0.9 ± 0.9 |
| 30% 2-OH-propyl-β-CD | 0 ± 0 | 0.4 ± 0.8 | −0.5 ± 1.3 | 1.2 ± 0.9 | 0.5 ± 1.2 | 0.7 ± 1.5 | 1.7 ± 1.5 |
| 0.25% Arachidonyl ethanolamide in 5.0% 2-OH-propyl-β-CD | 0 ± 0 | 2.1 ± 0.9 | −1.3 ± 2.5 | −4.4 ± 1.7 | −2.5 ± 1.2 | −0.5 ± 1.1 | −0.6 ± 0.9 |
| Untreated eye (contralateral) | | | | | | | |
| 0.9% NaCl | 0 ± 0 | −1.2 ± 0.4 | −1.7 ± 0.4 | 0.0 ± 0.7 | −0.3 ± 0.6 | 1.1 ± 0.7 | 1.7 ± 0.8 |
| 30% 2-OH-propyl-β-CD | 0 ± 0 | −0.1 ± 0.5 | −1.3 ± 0.6 | −0.5 ± 1.1 | −0.9 ± 0.4 | 0.2 ± 1.0 | −0.1 ± 0.7 |
| 0.25% Arachidonyl ethanolamide in 5.0% 2-OH-propyl-β-CD | 0 ± 0 | −1.1 ± 0.7 | −1.2 ± 0.6 | 0.4 ± 0.7 | 0.7 ± 0.8 | 0.8 ± 1.4 | 0.8 ± 0.5 |

As shown in FIGS. 3A and 3B, and Table II above, the unilateral intraocular administration of a 30% (w/v) solution of 2-OH-propyl-β-cyclodextrin alone does not greatly affect the IOP of treated or untreated (contralateral) eyes in normotensive albino rabbits when compared to administration of the 0.9% (w/v) NaCl solution.

Comparative Examples 4 to 6 below demonstrate the initial hypertensive phase present in the action of anandamide and certain analogues thereof, as well as their IOP lowering effects.

COMPARATIVE EXAMPLE 4

In this example, the effect of a 0.25% (w/v) arachidonyl ethanolamide solution on intraocular pressure (IOP) of normotensive pigmented (weighing between 2.1–3.6 kg, n=6) and albino (New Zealand strain) rabbits (weighing between 3.3–4.3 kg (n=4)) of both sexes was studied. The rabbits were housed separately in cages under standard laboratory conditions, i.e., 10 hr dark/14 hr light cycle.

More specifically, 12.5 mg of arachidonyl ethanolamide and 250 mg of 2-OH-propyl-β-CD were added to 5.0 ml of distilled water, and the solution was adjusted to pH 7.0 with sodium hydroxide/hydrochloric acid. Then, distilled water was added to adjust the total volume to 5.0 ml. The osmolality of the solution was adjusted to isotonic, 301 mOsm/kg, with sodium chloride.

As a control, a 0.9% (w/v) NaCl was also prepared.

Then, 25 μl of the drug-CD solution or the NaCl solution was administered unilaterally. Again, the rabbits were kept in restraint boxes during the study, and IOP was measured using a BioRad (Cambridge, Mass.) Digilab Modular One Pneumatonometer. Also, before each measurement, one or two drops of 0.06% (w/v) oxybuprocaine were applied to the cornea before tonometry to eliminate discomfort. For each determination at least two readings were taken from each eye. The measurements were started 2 hr before drug-CD or 0.9% (w/v) NaCl solution administration, and were continued 5 hr after administration.

The IOPs of pigmented and albino rabbits at the time of eyedrop administration were between 19.6–27.2 mmHg (n=6) and 12.4–23.8 mmHg (n=4), respectively.

The results are shown in FIGS. 4A and 4B, FIGS. 5A and 5B, and Table I above and Table II above. All of the values are expressed as the mean±standard error of means (X±S.E.).

Figure 4A:
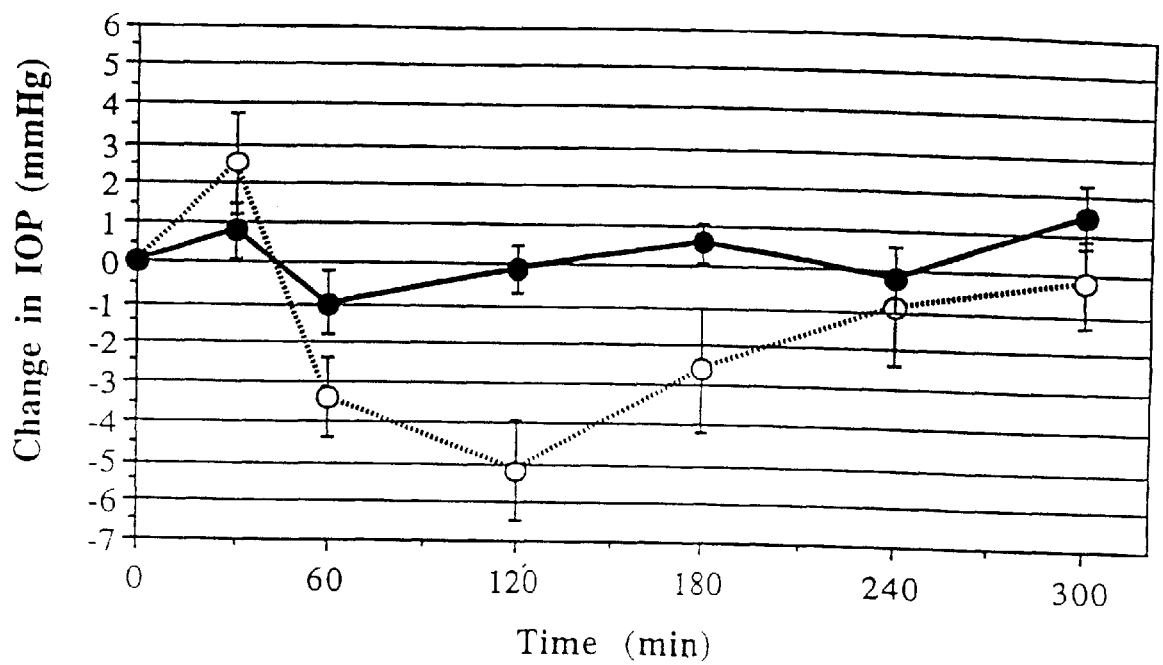
FIG. 4A shows the IOP changes in normotensive pigmented rabbits (treated eyes) after unilateral ocular administration (25 μl) of 0.25% (w/v) arachidonyl ethanolamide (○) or 0.9% (w/v) NaCl (•), mean±S.E. (n=6).

As shown in FIG. 4A and Table I above, unilateral intraocular administration of arachidonyl ethanolamide decreases the IOP in treated eyes in normotensive pigmented rabbits when compared to administration of the 0.9% (w/v) NaCl solution. In the treated eyes of normotensive pigmented rabbits, cyclodextrin vehiculated arachidonyl ethanolamide showed a hypertensive phase during the first 30 min, and a maximal IOP reduction of 5.2 mmHg, 2 hr after 0.25% (w/v) arachidonyl ethanolamide treatment.

Figure 4B:
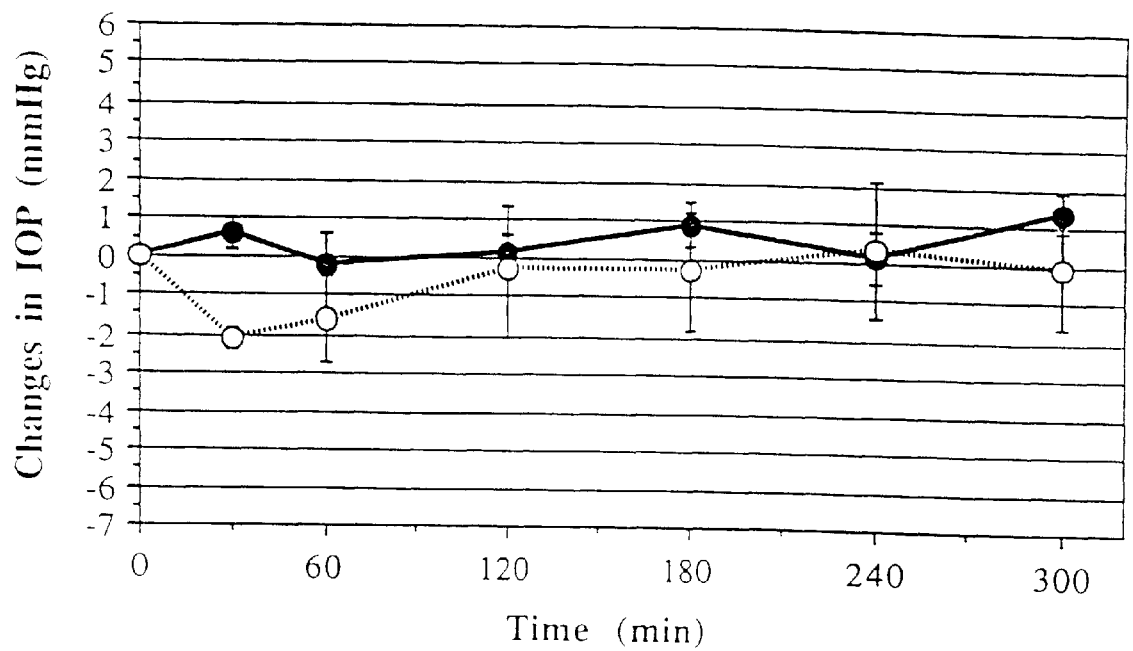
FIG. 4B shows the IOP changes in normotensive pigmented rabbits (untreated eyes) after unilateral ocular administration (25 1l) of 0.25% (w/v) arachidonyl ethanolamide (○) or 0.9% (w/v) NaCl (•), mean±S.E. (n=6).

On the other hand, as shown in FIG. 4B and Table I above, unilateral intraocular administration of arachidonyl ethanolamide does not greatly affect the IOP in the contralateral (untreated) eye in normotensive pigmented rabbits when compared to administration of the 0.9% (w/v) NaCl solution. Specifically, in the contralateral eye of normotensive pigmented rabbits, the maximal IOP reduction was 2.1 mmHg, 30 min after 0.25% (w/v) arachidonyl ethanolamide treatment.

Figure 5A:
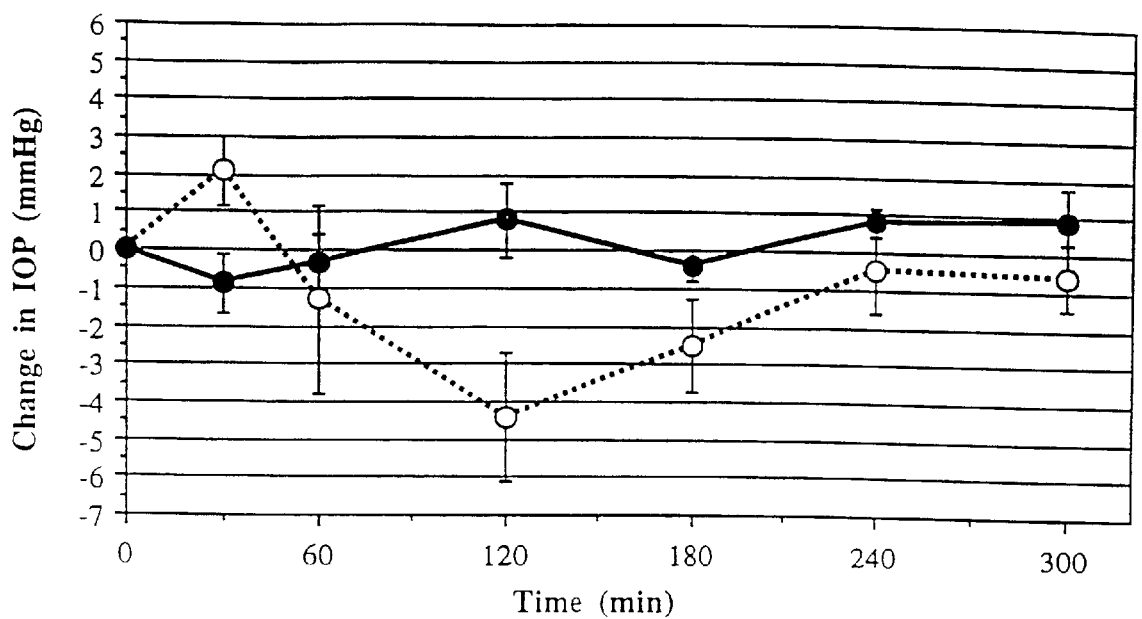
FIG. 5A shows the IOP changes in normotensive albino rabbits (treated eyes) after unilateral ocular administration (25 μl) of 0.25% (w/v) arachidonyl ethanolamide (○) or 0.9% (w/v) NaCl (•), means±S.E. (n=4).

Similarly, as shown in FIG. 5A and Table II above, unilateral intraocular administration of arachidonyl ethanolamide also resulted in a hypertensive peak at 30 min, thereafter decreasing the IOP in treated eyes in normotensive albino rabbits when compared to administration of the 0.9% (w/v) NaCl solution. Specifically, in the treated eyes of normotensive albino rabbits, cyclodextrin vehiculated arachidonyl ethanolamide showed a maximal IOP reduction of 4.4 mmHg, 2 hr after 0.25% (w/v) arachidonyl ethanolamide treatment.

Figure 5B:
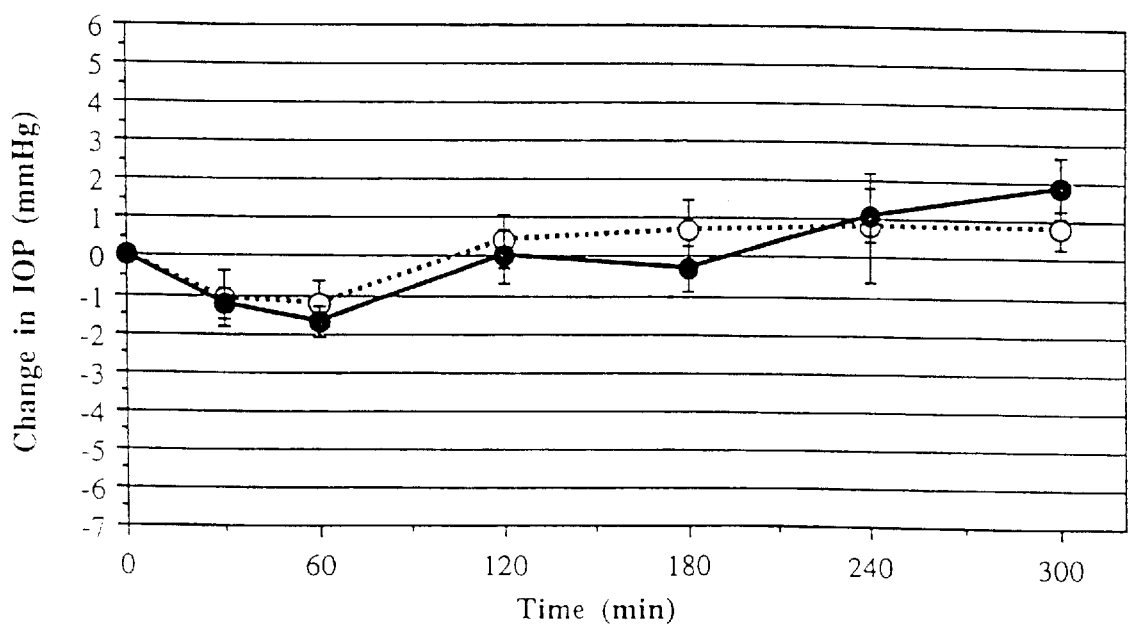
FIG. 5B shows the IOP changes in normotensive albino rabbits (untreated eyes) after unilateral ocular administration (25 μl) of 0.25% (w/v) arachidonyl ethanolamide (○) or 0.9% (w/v) NaCl (•), means±S.E. (n=4).

However, as shown in FIG. 5B and Table II above, no great affect on the IOP in the contralateral (untreated) eye in normotensive albino rabbits was seen when compared to administration of the 0.9% (w/v) NaCl solution. In particular, in the contralateral eye of normotensive pigmented rabbits, the maximal IOP reduction was 1.3 mmHg, 60 min after 0.25% (w/v) arachidonyl ethanolamide treatment.

COMPARATIVE EXAMPLE 5

In this example, the effect of a 0.25% (w/v) arachidonyl propanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl propanolamide and 375 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 298 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 14.0–29.7 mmHg (n=6).

Figure 6A:
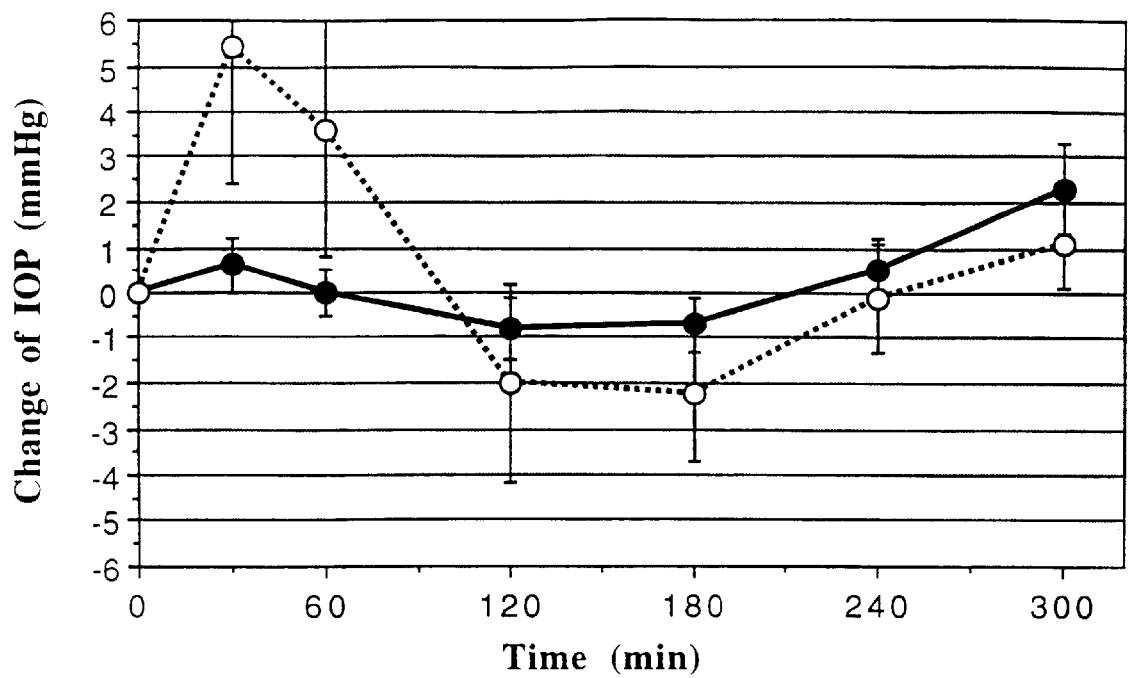
FIG. 6A shows the IOP changes in normotensive pigmented rabbits (treated eyes) after unilateral ocular administration (25 μl) of 0.25% (w/v) arachidonyl propanolamide (○) or 0.9% (w/v) NaCl (•), mean±S.E. (n=6).
Figure 6B:
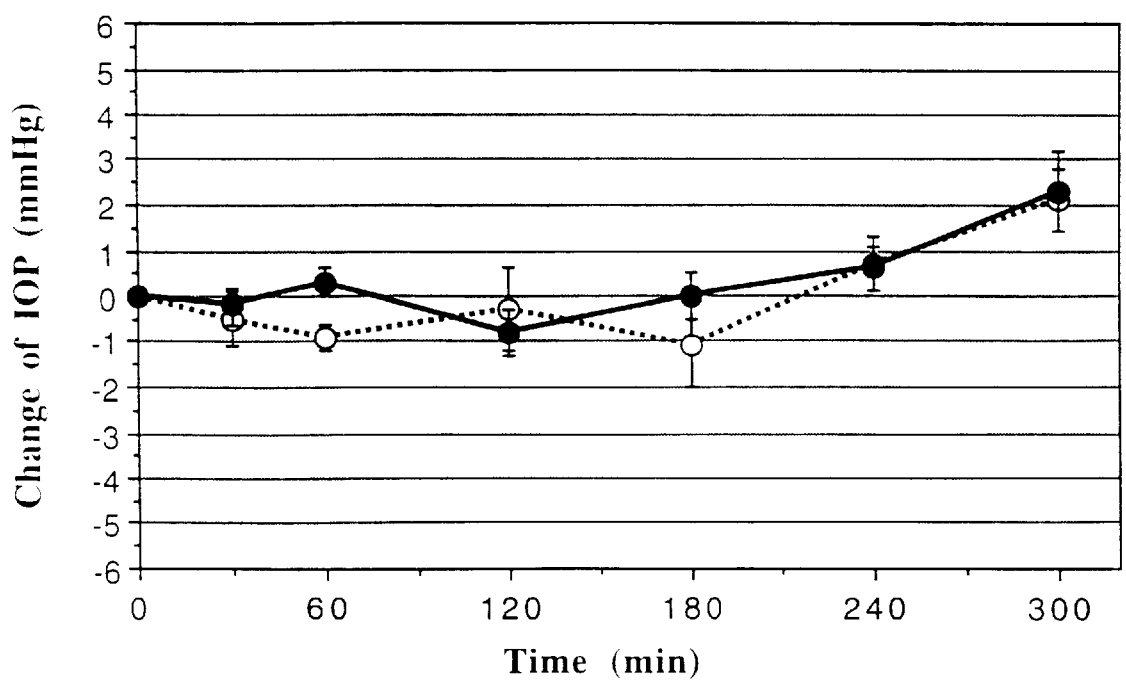
FIG. 6B shows the IOP changes in normotensive pigmented rabbits (untreated eyes) after unilateral ocular administration (25 μl) of 0.25% (w/v) arachidonyl propanolamide (○) or 0.9% (w/v) NaCl (•) mean±S.E. (n=6).

The results are shown in FIGS. 6A and 6B, and Table III below. All of the values are expressed as the mean±standard error of means (X±S.E.).

3 hr after 0.25% (w/v) arachidonyl propanolamide treatment, but preceded by a severe hypertensive phase lasting almost 2 hr.

However, as shown in FIG. 6B and Table III above, unilateral ocular administration of arachidonyl propanolamide does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.1 mmHg, 3 hr after 0.25% (w/v) arachidonyl propanolamide treatment.

COMPARATIVE EXAMPLE 6

In this example, the effect of a 0.25% (w/v) arachidonyl fluoroethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl fluoroethylamide and 750 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 310 mOsm/kg, with sodium chloride.

TABLE III

Intraocular Pressure Changes (mmHg) at Predetermined Times (h) in Normotensive Pigmented Rabbits After Unilateral Administration of Eyedrops (mean ± S.E., n = 5–6)

| Solution | 0 h | 0.5 h | 1 h | 2 h | 3 h | 4 h | 5 h |
|---|---|---|---|---|---|---|---|
| *Treated eye* | | | | | | | |
| 0.9% NaCl | 0 ± 0 | 0.7 ± 1.0 | 1.0 ± 0.8 | −0.3 ± 0.6 | 0.6 ± 1.0 | 3.5 ± 1.7 | 3.2 ± 1.0 |
| 0.25% Arachidonyl propanolamide in 7.5% 2-OH-propyl-β-CD | 0 ± 0 | 5.4 ± 3.0 | 3.6 ± 2.8 | −2.0 ± 2.2 | −2.2 ± 1.5 | −0.1 ± 1.2 | 1.1 ± 1.0 |
| 0.25% Arachidonyl fluoroethylamide in 15% in 2-OH-propyl-β-CD | 0 ± 0 | 1.7 ± 2.2 | 0.2 ± 1.7 | −3.7 ± 0.8 | −1.7 ± 0.6 | −0.3 ± 0.6 | −0.5 ± 0.6 |
| 0.25% Arachidonyl ethanethiolamide in 10% 2-OH-propyl-β-CD) | 0 ± 0 | −0.6 ± 0.9 | −0.9 ± 1.0 | −2.3 ± 0.4 | 0.0 ± 0.0 | −2.2 ± 1.0 | −2.4 ± 0.5 |
| *Untreated eye (contralateral)* | | | | | | | |
| 0.9% NaCl | 0 ± 0 | −1.1 ± 0.8 | 1.9 ± 1.7 | 1.1 ± 0.7 | −0.3 ± 1.2 | 1.9 ± 1.3 | 1.9 ± 0.7 |
| 0.25% Arachidonyl propanolamide in 7.5% in 2-OH-propyl-β-CD | 0 ± 0 | −0.5 ± 0.6 | −0.9 ± 0.3 | −0.3 ± 0.9 | −1.1 ± 0.9 | 0.7 ± 0.6 | 2.1 ± 0.7 |
| 0.25% Arachidonyl fluoroethylamide in 15% 2-OH-propyl-β-CD | 0 ± 0 | −0.3 ± 1.2 | −0.7 ± 0.9 | −1.2 ± 1.0 | −0.7 ± 1.0 | −1.3 ± 1.0 | 0.0 ± 1.0 |
| 0.25% Arachidonyl ethanethiolamide in 10% 2-OH-propyl-β-CD | 0 ± 0 | −2.0 ± 0.6 | −0.9 ± 0.3 | −0.1 ± 1.1 | 0.0 ± 0.0 | −0.6 ± 0.8 | 0.2 ± 1.0 |

As shown in FIG. 6A and Table III above, unilateral ocular administration of arachidonyl propanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl propanolamide showed a maximal IOP reduction of 2.2 mmHg, As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 15.2–21.6 mmHg (n=6).

Figure 7A:
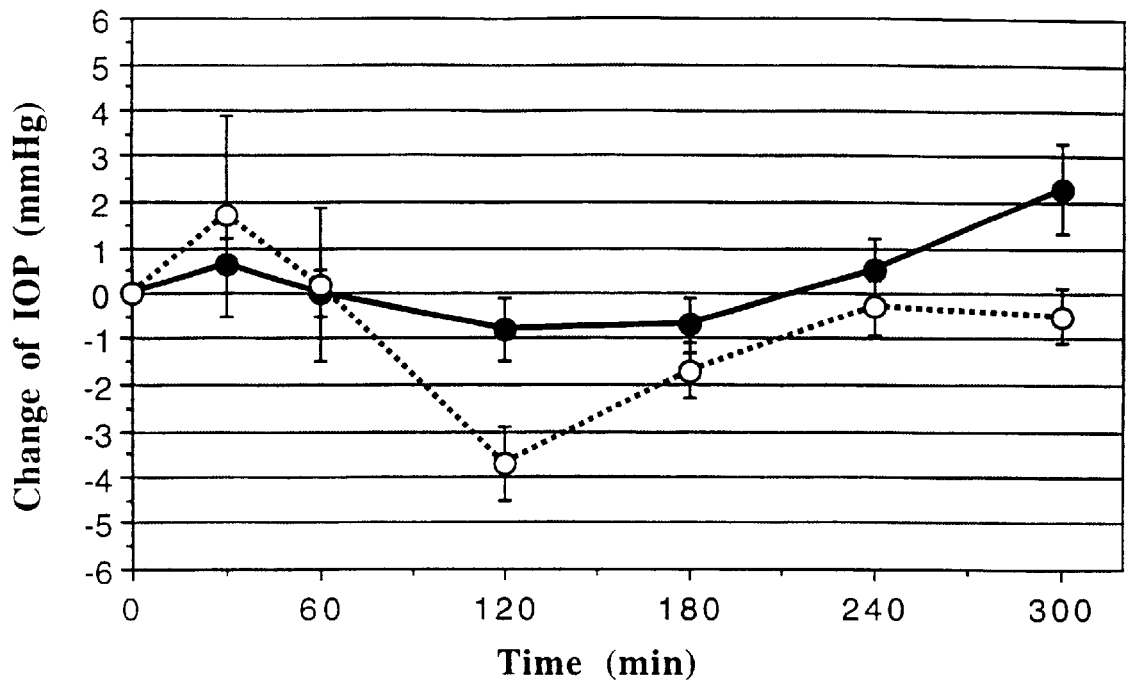
FIG. 7A shows the IOP changes in normotensive pigmented rabbits (treated eyes) after unilateral ocular administration (25 μl) of 0.25% (w/v) arachidonyl fluoroethylamide (○) or 0.9% (w/v) NaCl (•), means±S.E. (n=6).
Figure 7B:
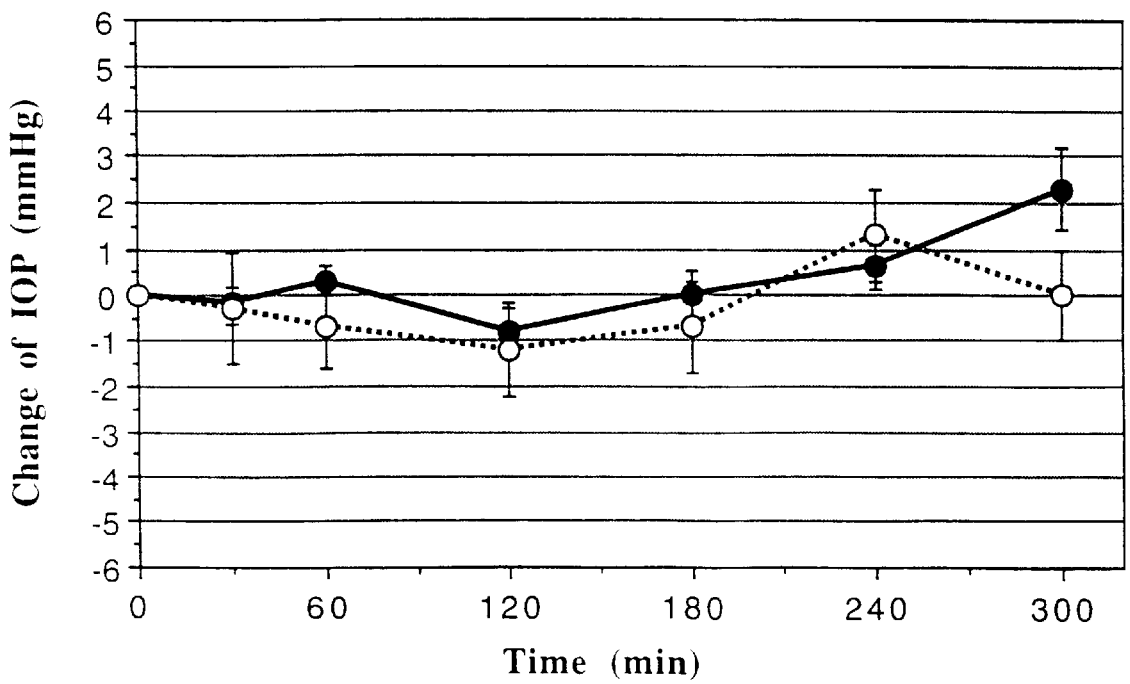
FIG. 7B shows the IOP changes in normotensive pigmented rabbits (untreated eyes) after unilateral ocular administration (25 μl) of 0.25% (w/v) arachidonyl fluoroethylamide (○) or 0.9% (w/v) NaCl (•), means±S.E. (n=5).

The results are shown in FIGS. 7A and 7B, and Table III above. All of the values are expressed as mean±standard error of means (X±S.E.).

As shown in FIG. 7A and Table III above, unilateral ocular administration of arachidonyl fluoroethylamide initially increases, and then decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl fluoroethylamide showed a maximal IOP reduction of 3.7 mmHg, 2 hr after 0.25% (w/v) arachidonyl fluoroethylamide treatment.

However, as shown in FIG. 7B and Table III above, unilateral ocular administration does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.2 mmHg, 2 hr after 0.25% (w/v) arachidonyl fluoroethylamide treatment.

COMPARATIVE EXAMPLE 7

In this example, the effect of a 0.25% (w/v) arachidonyl methoxyethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl methoxyethylamide and 750 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 317 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 22.6–25.9 mmHg (n=6).

Figure 8A:
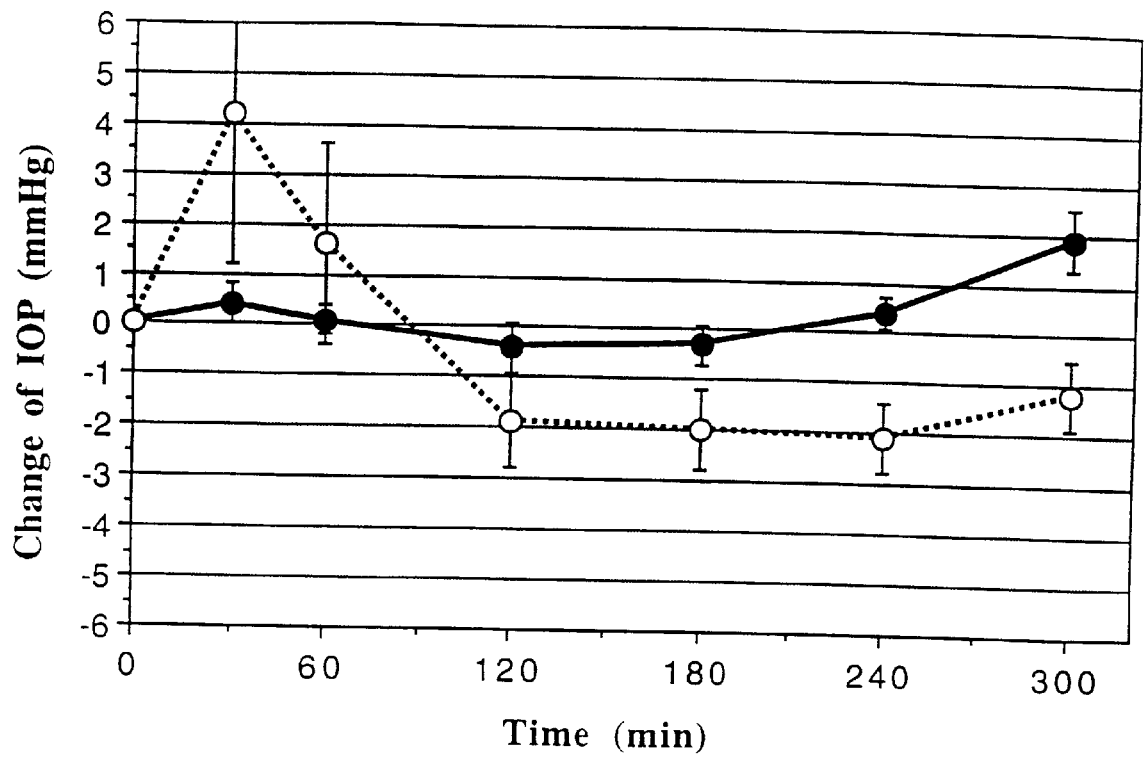
FIG. 8A shows the IOP changes in normotensive pigmented rabbits (treated eyes) after unilateral ocular administration (25 μl) of 0.25% (w/v) arachidonyl methoxyethylamide (○) or 0.9% (w/v) NaCl (•), mean±S.E. (n=6).
Figure 8B:
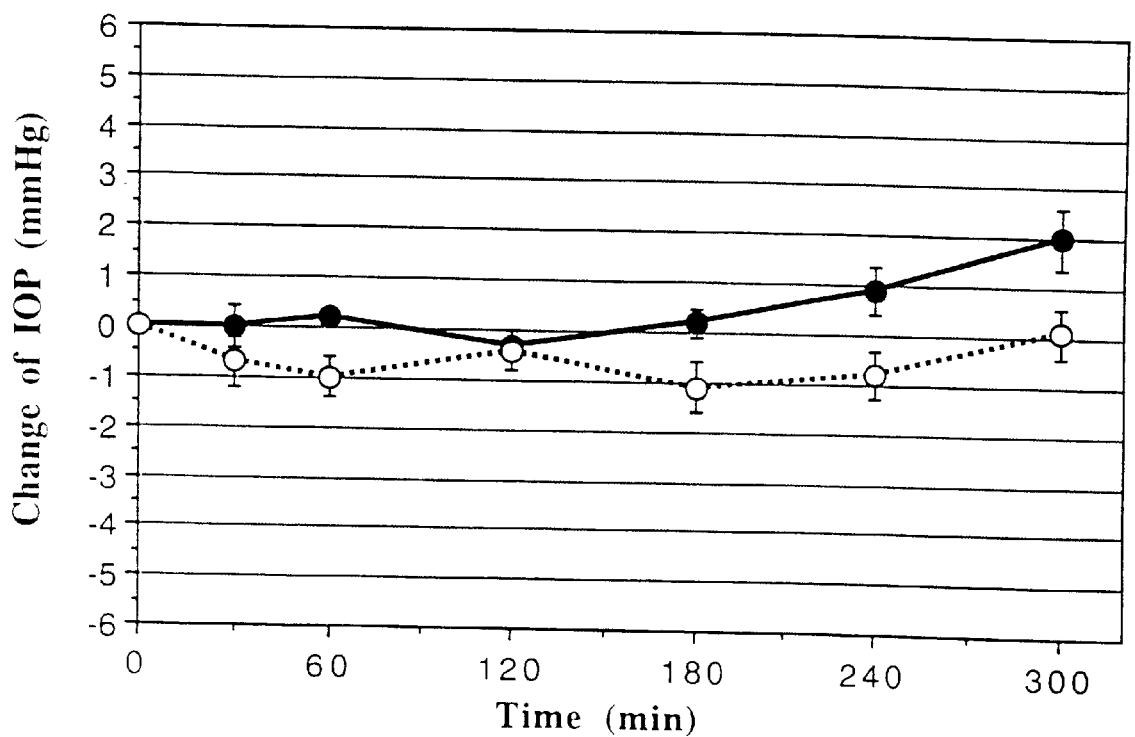
FIG. 8B shows the IOP changes in normotensive pigmented rabbits (untreated eyes) after unilateral ocular administration (25 μl) of 0.25% (w/v) arachidonyl methoxyethylamide (○) or 0.9% (w/v) NaCl (•), mean±S.E. (n=6).

The results are shown in FIGS. 8A and 8B, and Table IV below. All of the values are expressed as mean±standard error of means (X±S.E.).

TABLE IV

Intraocular Pressure Changes (mmHg) at Predetermined Times (h) in Normotensive Pigmented Rabbits After Unilateral Administration of Eyedrops (mean ± S.E., n = 6)

| Solution | 0 h | 0.5 h | 1 h | 2 h | 3 h | 4 h | 5 h |
|---|---|---|---|---|---|---|---|
| | | | Treated eye | | | | |
| 0.9% NaCl | 0 ± 0 | 0.4 ± 0.0 | 0.1 ± 0.3 | −0.4 ± 0.5 | −0.3 ± 0.4 | 0.4 ± 0.3 | 1.9 ± 0.6 |
| Arachidonyl methoxyethylamide | 0 ± 0 | 4.2 ± 3.0 | 1.6 ± 2.0 | −1.9 ± 0.9 | −2.0 ± 0.8 | −2.1 ± 0.7 | −1.2 ± 0.7 |
| Arachidonyl β-phenethylamide | 0 ± 0 | 1.1 ± 0.9 | −0.1 ± 0.7 | −0.3 ± 1.2 | −1.0 ± 0.7 | −1.0 ± 0.7 | −0.5 ± 1.0 |
| Arachidonyl aminoethylamide | 0 ± 0 | −0.8 ± 1.0 | −2.0 ± 0.8 | −1.5 ± 0.8 | −1.6 ± 0.8 | −0.3 ± 0.9 | −0.1 ± 1.5 |
| Arachidonyl N,N-dimethylamino ethanolamide | 0 ± 0 | 0.2 ± 0.3 | 0.3 ± 0.5 | 0.1 ± 0.7 | −0.1 ± 0.5 | −0.8 ± 0.6 | 0.6 ± 0.5 |
| Arachidonyl N-acetyl aminoethylamide | 0 ± 0 | 0.8 ± 2.1 | −0.1 ± 1.6 | −0.8 ± 0.5 | −0.7 ± 0.4 | −1.0 ± 0.3 | 0.2 ± 0.6 |
| Arachidonyl pyridinoethylamide | 0 ± 0 | 0.7 ± 2.2 | −0.7 ± 1.1 | −2.2 ± 0.9 | −1.8 ± 0.6 | −1.4 ± 0.5 | −0.9 ± 0.8 |
| Arachidonyl propionitrileamide | 0 ± 0 | 0.8 ± 2.3 | −0.7 ± 2.3 | −3.3 ± 1.3 | −3.9 ± 1.2 | −2.1 ± 0.6 | 0.5 ± 0.6 |
| Arachidonyl morpholineamide | 0 ± 0 | −0.6 ± 0.9 | −1.4 ± 0.8 | 0.1 ± 0.6 | −0.2 ± 0.8 | 0.7 ± 0.6 | 1.2 ± 0.5 |
| Arachidonyl α-dimethyl ethanolamide | 0 ± 0 | −0.4 ± 0.4 | −1.9 ± 0.8 | −2.5 ± 0.9 | −1.8 ± 0.7 | −0.6 ± 0.8 | 1.4 ± 0.6 |
| Arachidonyl α-isopropyl ethanolamide | 0 ± 0 | −1.9 ± 0.7 | −2.7 ± 0.5 | −3.8 ± 0.6 | −3.6 ± 0.5 | −1.4 ± 0.8 | −0.9 ± 0.6 |
| Arachidonyl α-phenyl ethanolamide | 0 ± 0 | −0.1 ± 0.6 | −0.1 ± 0.6 | −0.9 ± 0.4 | −0.5 ± 0.6 | −0.5 ± 0.7 | 0.7 ± 0.6 |

TABLE IV-continued

Intraocular Pressure Changes (mmHg) at Predetermined Times (h) in
Normotensive Pigmented Rabbits After Unilateral Administration of Eyedrops
(mean ± S.E., n = 6)

| Solution | 0 h | 0.5 h | 1 h | 2 h | 3 h | 4 h | 5 h |
|---|---|---|---|---|---|---|---|
| Untreated eye (contralateral) | | | | | | | |
| 0.9% NaCl | 0 ± 0 | 0.0 ± 0.4 | 0.2 ± 0.1 | −0.3 ± 0.3 | 0.2 ± 0.3 | 0.9 ± 0.5 | 2.0 ± 0.6 |
| Arachidonyl methoxyethylamide | 0 ± 0 | −0.7 ± 0.5 | −1.0 ± 0.4 | −0.4 ± 0.4 | −1.1 ± 0.5 | −0.8 ± 0.5 | 0.1 ± 0.5 |
| Arachidonyl β-phenethylamide | 0 ± 0 | −0.1 ± 0.6 | −0.6 ± 0.6 | −0.7 ± 0.5 | −0.9 ± 0.8 | −1.2 ± 0.5 | 0.5 ± 0.8 |
| Arachidonyl aminoethylamide | 0 ± 0 | −0.3 ± 0.6 | −1.2 ± 0.7 | −1.1 ± 0.6 | −1.7 ± 1.0 | 0.1 ± 0.7 | 0.5 ± 1.2 |
| Arachidonyl N,N-dimethylamino ethanolamide | 0 ± 0 | −0.4 ± 0.2 | −0.6 ± 0.5 | −0.8 ± 0.4 | −1.2 ± 0.6 | −1.0 ± 0.5 | 0.5 ± 0.8 |
| Arachidonyl N-acetyl aminoethylamide | 0 ± 0 | −1.1 ± 0.7 | −1.4 ± 0.5 | −1.0 ± 0.6 | −1.3 ± 0.5 | −0.7 ± 0.4 | 0.1 ± 0.6 |
| Arachidonyl pyridinoethylamide | 0 ± 0 | −0.8 ± 0.6 | −1.6 ± 0.8 | −1.9 ± 0.8 | −1.9 ± 0.7 | −1.4 ± 0.8 | −0.9 ± 1.2 |
| Arachidonyl propionitrileamide | 0 ± 0 | −0.9 ± 0.5 | −2.0 ± 0.6 | −1.2 ± 0.7 | −2.1 ± 0.7 | −1.5 ± 0.4 | 0.3 ± 0.6 |
| Arachidonyl morpholineamide | 0 ± 0 | −0.7 ± 0.7 | −0.4 ± 0.6 | 0.2 ± 0.3 | −1.1 ± 0.4 | 0.0 ± 0.3 | 0.4 ± 0.3 |
| Arachidonyl α-dimethyl ethanolamide | 0 ± 0 | −0.6 ± 0.5 | −1.4 ± 0.4 | −1.7 ± 1.0 | −1.4 ± 0.8 | −0.3 ± 1.0 | 1.1 ± 0.5 |
| Arachidonyl α-isopropyl ethanolamide | 0 ± 0 | −1.0 ± 0.6 | −1.7 ± 0.6 | −3.0 ± 0.6 | −3.7 ± 0.4 | −1.2 ± 0.7 | −0.8 ± 0.3 |
| Arachidonyl α-phenyl ethanolamide | 0 ± 0 | −0.4 ± 0.6 | 0.2 ± 0.7 | −0.9 ± 1.0 | −1.4 ± 0.7 | −0.2 ± 0.8 | 0.7 ± 0.5 |

As shown in FIG. 8A and Table IV above, unilateral ocular administration of arachidonyl methoxyethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl methoxyethylamide showed a severe IOP increase lasting approximately 90 min before the maximal IOP reduction of 2.1 mmHg, 4 hr after 0.25% (w/v) arachidonyl methoxyethylamide treatment.

However, as shown in FIG. 8B and Table IV above, unilateral ocular administration does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.1 mmHg, 3 hr after 0.25% (w/v) arachidonyl methoxyethylamide treatment.

The results in the foregoing examples clearly demonstrate that unilateral intraocular administration of a fatty acid alkanol amide of the type taught in PCT WO 94/12466, such as arachidonyl ethanolamide or arachidonyl propanolamide, in a cyclodextrin, as well as other anandamides, such as arachidonyl fluoroethylamide and arachidonyl methoxyethylamide, decreases the IOP in treated eyes in normotensive pigmented (FIGS. 4A, 6A, 7A and 8A, and Tables I, III and IV) and albino rabbits (FIG. 5A and Table II) when compared to administration of the 0.9% (w/v) NaCl solution, but induces an initial hypertensive peak of a potentially deleterious nature when employed clinically. In the treated eyes of normotensive pigmented rabbits, cyclodextrin vehiculated arachidonyl ethanolamide showed an IOP rise of 2.5 mmHg at 30 min, and then a maximal IOP reduction of 5.2 mmHg, 2 hr after 0.25% (w/v) arachidonyl ethanolamide treatment. The maximal IOP reduction in normotensive albino rabbits was 4.4 mmHg, 2 hr after 0.25% (w/v) arachidonyl ethanolamide treatment, but preceded by a similar (2.1 mmHg) hypertensive phase.

In the treated eyes of normotensive pigmented rabbits, cyclodextrin vehiculated arachidonyl methoxyethylamide showed an IOP elevation (maximum 4.2 mmHg) for more than 1 hr after 0.25% (w/v) arachidonyl methoxyethylamide treatment, and arachidonyl propanolamide showed an IOP elevation (maximum 5.4 mmHg) for almost 2 hr after 0.25% (w/v) arachidonyl propanolamide treatment.

Furthermore, these results show that the unilateral ocular administration of 2-OH-propyl-β-cyclodextrin (5.0% (w/v), 12.5% (w/v) and 30% (w/v)) alone does not affect the IOP of treated or untreated (contralateral) eyes in normotensive rabbits (FIGS. 1A, 1B, 2A, 2B, 3A and 3B; and Tables I and II) when compared to administration of the 0.9% (w/v) NaCl solution.

Moreover, the results show that with cyclodextrins it is possible to achieve effective ocular delivery of very lipophilic and water-insoluble compounds, like anandamides, from aqueous eye drop formulations. The cyclodextrins increase the ocular bioavailability of anandamides by increasing the aqueous solubility of anandamides in solution and in the tear-fluid on the precorneal area. The concentration and type of cyclodextrin in the composition of the present invention can be readily selected according to a concentration and type of anandamide employed.

Examples 1 to 8 below demonstrate that certain modifications of the terminal amide moiety, according to Formula (I), ameliorate the characteristic hypertensive phase seen by the above anandamides.

EXAMPLE 1

In this example, the effect of a 0.25% (w/v) arachidonyl ethanethiolamide solution on IOP of normotensive pigmented rabbits weighing between 2.6–3.6 kg (n=5) was studied. The rabbits were housed separately in cages under standard laboratory conditions, i.e., 10 hr dark/14 hr light cycle.

More specifically, 12.5 mg of arachidonyl ethanethiolamide and 500 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 325 mOsm/kg, with sodium chloride.

As a control, a 0.9% (w/v) NaCl was also prepared.

Then, 25 µl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The iOPs of the pigmented rabbits at the time of eyedrop administration were between 17.1–27.7 mmHg (n=5).

Figure 9A:
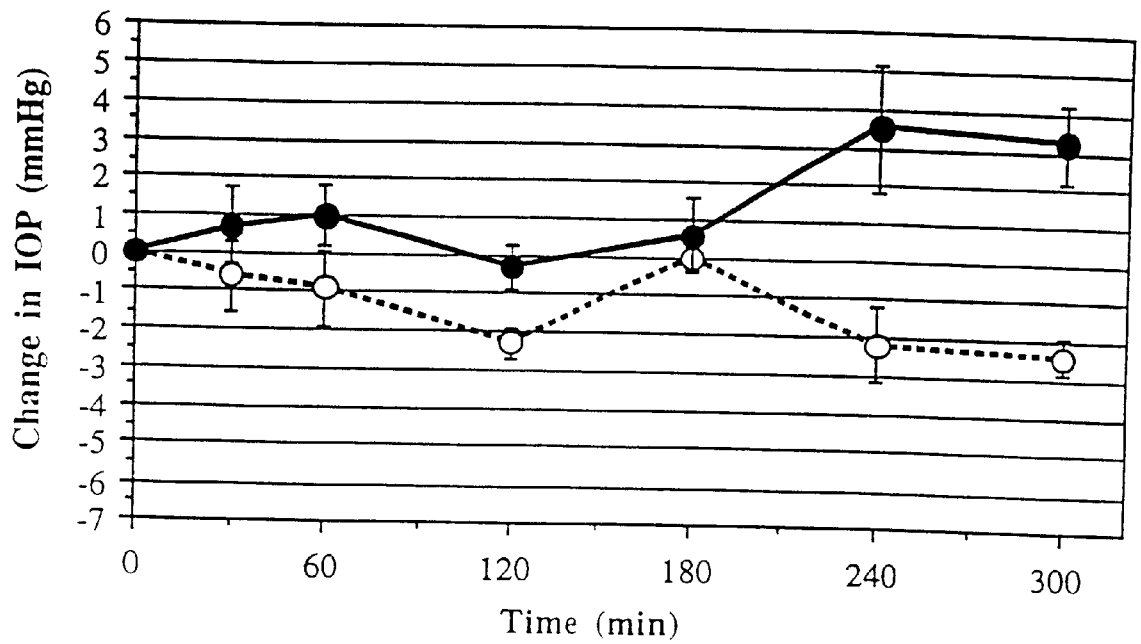
FIG. 9A shows the IOP changes in normotensive pigmented rabbits (treated eyes) after unilateral ocular administration (25 μl) of 0.25% (w/v) arachidonyl ethanethiolamide (○) or 0.9% (w/v) NaCl (•), means±S.E. (n=5).
Figure 9B:
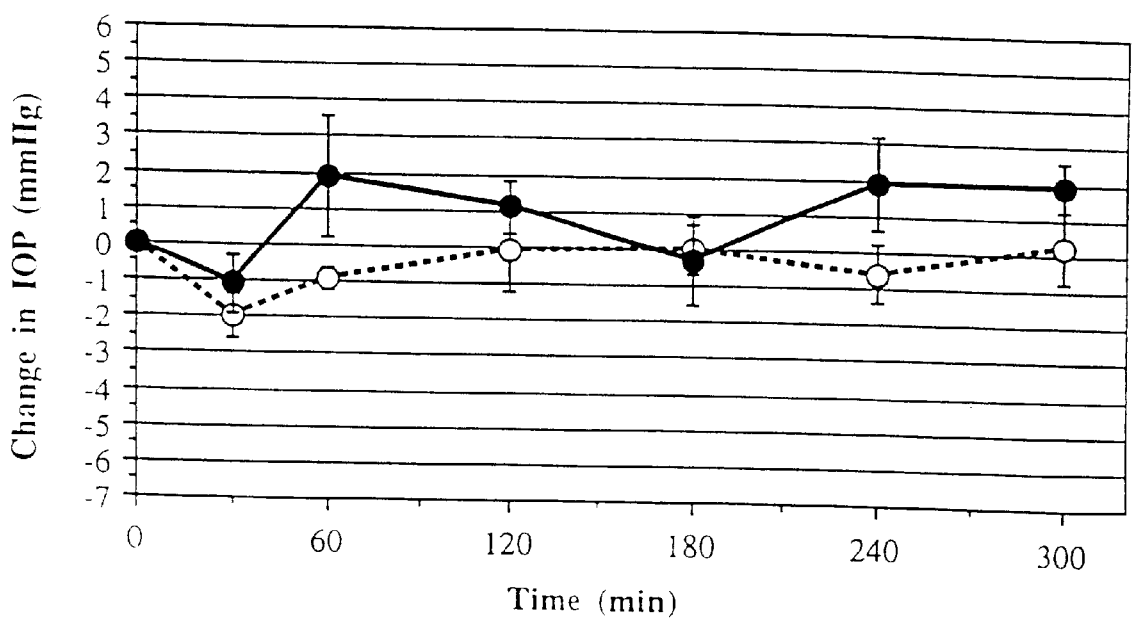
FIG. 9B shows the IOP changes in normotensive pigmented rabbits (untreated eyes) after unilateral ocular administration (25 μl) of 0.25% (w/v) arachidonyl ethanethiolamide (○) or 0.9% (w/v) NaCl (•), means±S.E. (n=5).

The results are shown in FIGS. 9A and 9B, and Table III above. All of the values are expressed as mean±standard error of means (X±S.E.).

As shown in FIG. 9A and Table III above, unilateral ocular administration of arachidonyl ethanethiolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl ethanethiolamide showed a maximal IOP reduction of 2.4 mmHg, 5 hr after 0.25% (w/v) arachidonyl ethanethiolamide treatment.

However, as shown in FIG. 9B and Table III above, unilateral ocular administration does not greatly affect the IOP in the contralateral (untreated) eye in normotensive pigmented rabbits when compared to administration of the 0.9% (w/v) NaCl solution. In the contralateral eye of normotensive pigmented rabbits, the maximal IOP reduction was 2.0 mmHg, 30 min after 0.25% (w/v) arachidonyl ethanethiolamide treatment.

EXAMPLE 2

In this example, the effect of a 0.20% (w/v) arachidonyl β-phenethylamide solution on the IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 10 mg of arachidonyl β-phenethylamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 310 mOsm/kg, with sodium chloride.

As a control, a 0.9% (w/v) NaCl was also prepared.

Then, 25 µl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 19.5–28.6 mmHg (n=6).

Figure 10A:
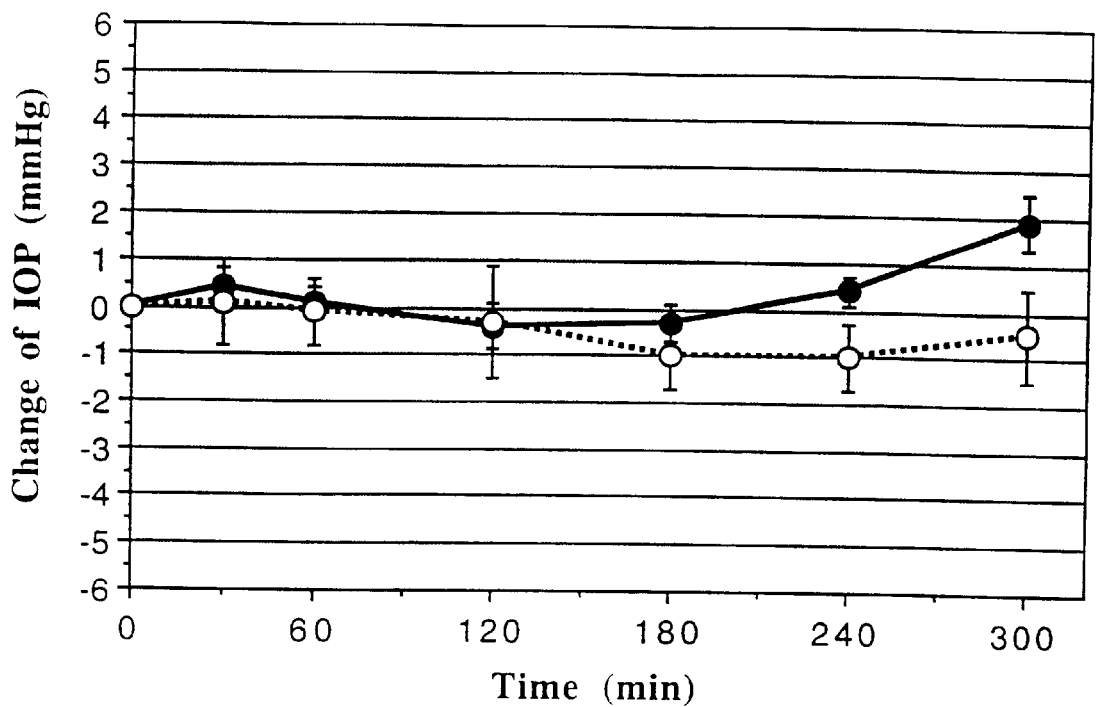
FIG. 10A shows the IOP changes in normotensive pigmented rabbits (treated eyes) after unilateral ocular administration (25 μl) of 0.20% (w/v) arachidonyl β-phenethylamide (○) or 0.9% (w/v) NaCl (•), mean±S.E. (n=6).
Figure 10B:
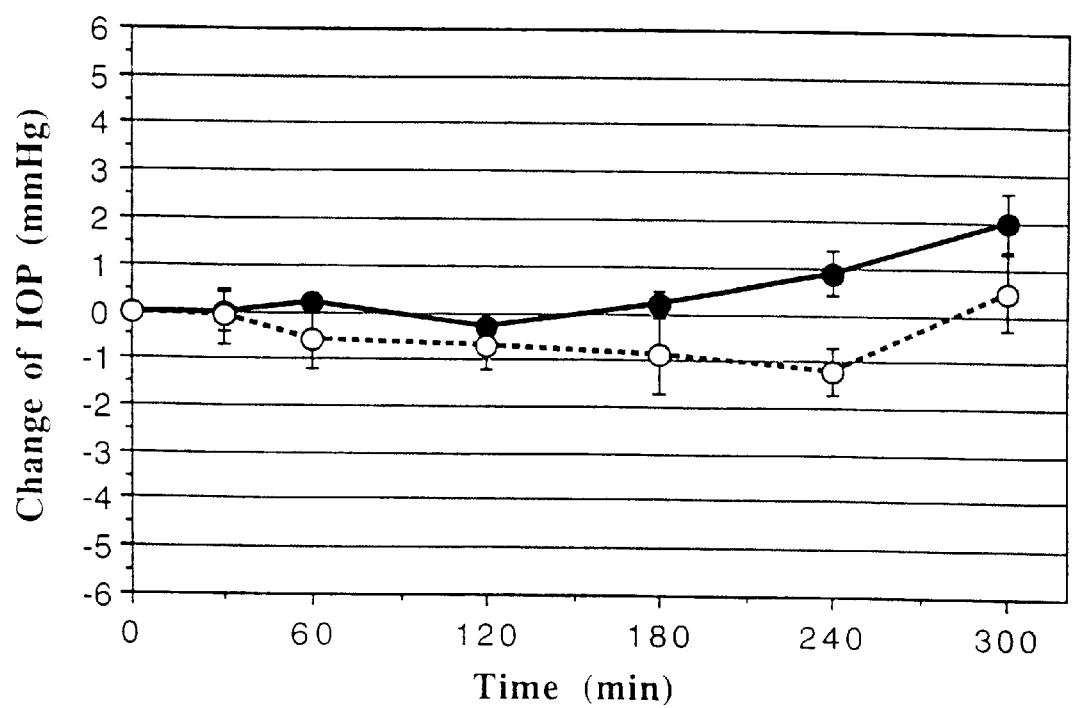
FIG. 10B shows the IOP changes in normotensive pigmented rabbits (untreated eyes) after unilateral ocular administration (25 μl) of 0.20% (w/v) arachidonyl β-phenethylamide (○) or 0.9% (w/v) NaCl (•), mean±S.E. (n=6).

The results are shown in FIGS. 10A and 10B, and Table IV above. All of the values are expressed as mean±standard error of means (X±S.E.).

As shown in FIG. 10A and Table IV above, unilateral ocular administration of arachidonyl β-phenethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl β-phenethylamide showed a maximal IOP reduction of 1.0 mmHg, 3–4 hr after 0.2% (w/v) arachidonyl β-phenethylamide treatment.

However, as shown in FIG. 10B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.2 mmHg, 4 hr after 0.2% (w/v) arachidonyl β-phenethylamide treatment.

EXAMPLE 3

In this example, the effect of a 0.25% (w/v) arachidonyl aminoethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl aminoethylamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 390 mOsm/kg, with sodium chloride.

As a control, a 0.9% (w/v) NaCl was also prepared.

Then, 25 µl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 21.7–26.4 mmHg (n=6).

Figure 11A:
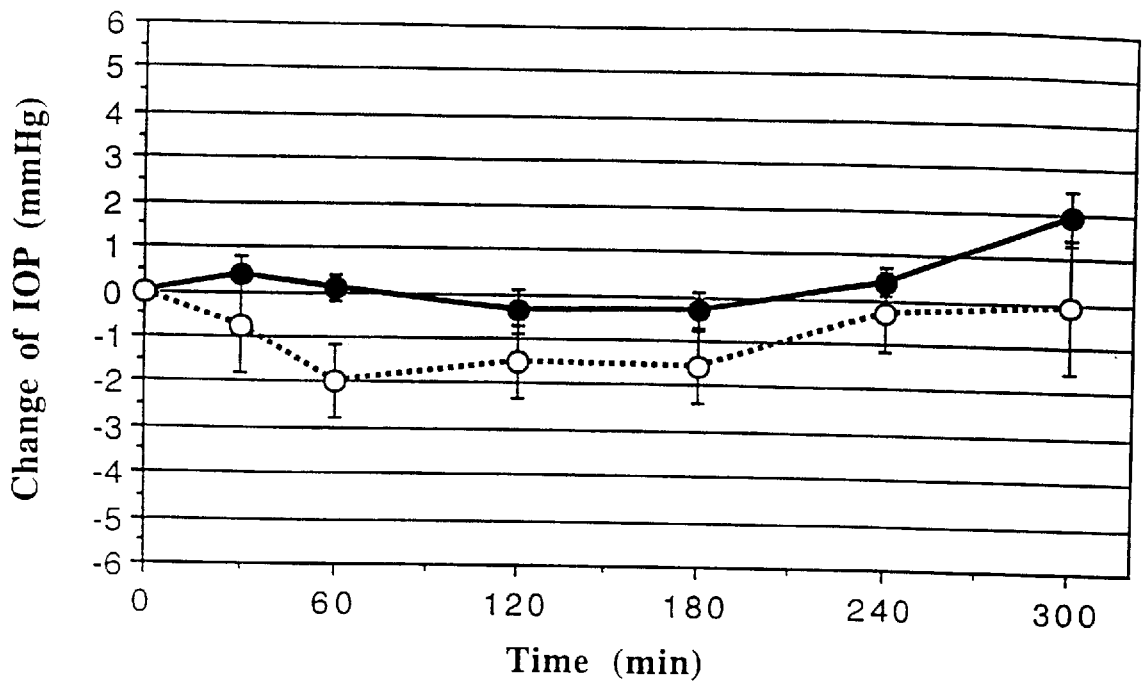
FIG. 11A shows the IOP changes in normotensive pigmented rabbits (treated eyes) after unilateral ocular administration (25 μl) of 0.25% (w/v) arachidonyl aminoethylamide (○) or 0.9% (w/v) NaCl (•), mean±S.E. (n=6).
Figure 11B:
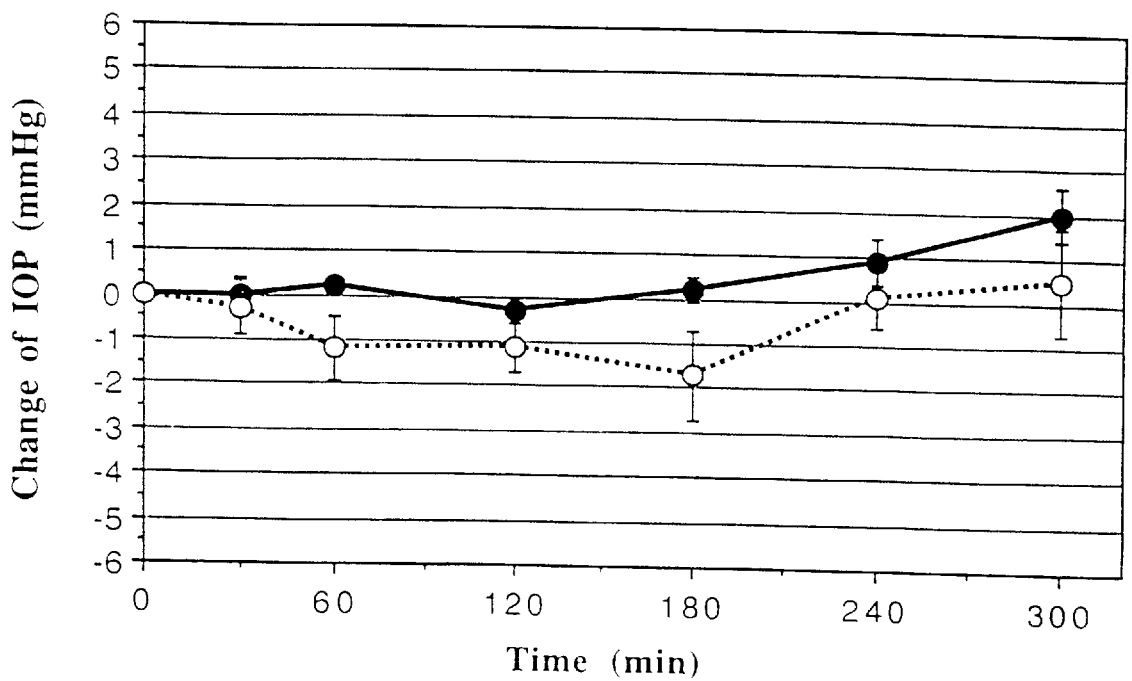
FIG. 11B shows the IOP changes in normotensive pigmented rabbits (untreated eyes) after unilateral ocular administration (25 μl) of 0.25% (w/v) arachidonyl aminoethylamide (○) or 0.9% (w/v) NaCl (•), mean±S.E. (n=6).

The results are shown in FIGS. 11A and 11B, and Table IV above. All of the values are expressed as mean±standard error of means (X±S.E.).

As shown in FIG. 11A and Table IV above, unilateral ocular administration of arachidonyl aminoethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl aminoethylamide showed a maximal IOP reduction of 2.0 mmHg, 1 hr after 0.25% (w/v) arachidonyl aminoethylamide treatment.

However, as shown in FIG. 11B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.7 mmHg, 3 hr after 0.25% (w/v) arachidonyl aminoethylamide treatment.

EXAMPLE 4

In this example, the effect of a 0.20% (w/v) arachidonyl N,N-dimethylaminoethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 10.0 mg of arachidonyl N,N-dimethylaminoethylamide and 1250 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 303 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 19.9–25.6 mmHg (n=6).

Figure 12A:
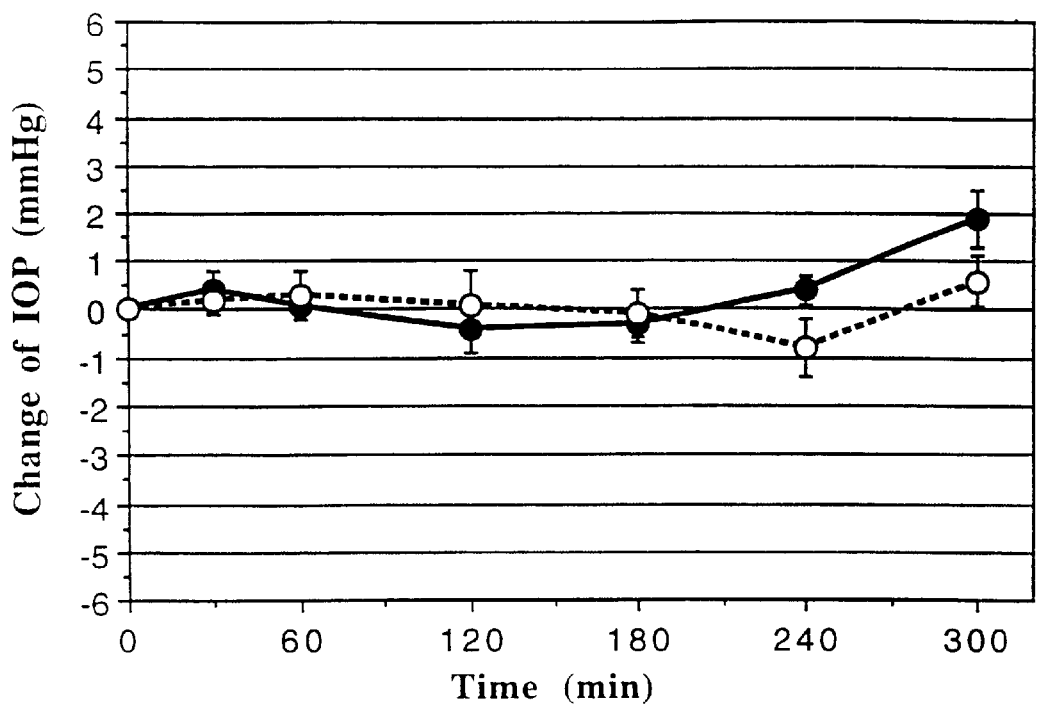
FIG. 12A shows the IOP changes in normotensive pigmented rabbits (treated eyes) after unilateral ocular administration (25 μl) of 0.20% (w/v) arachidonyl N,N-dimethylaminoethylamide (○) or 0.9% (w/v) NaCl (•), mean±S.E. (n=6).
Figure 12B:
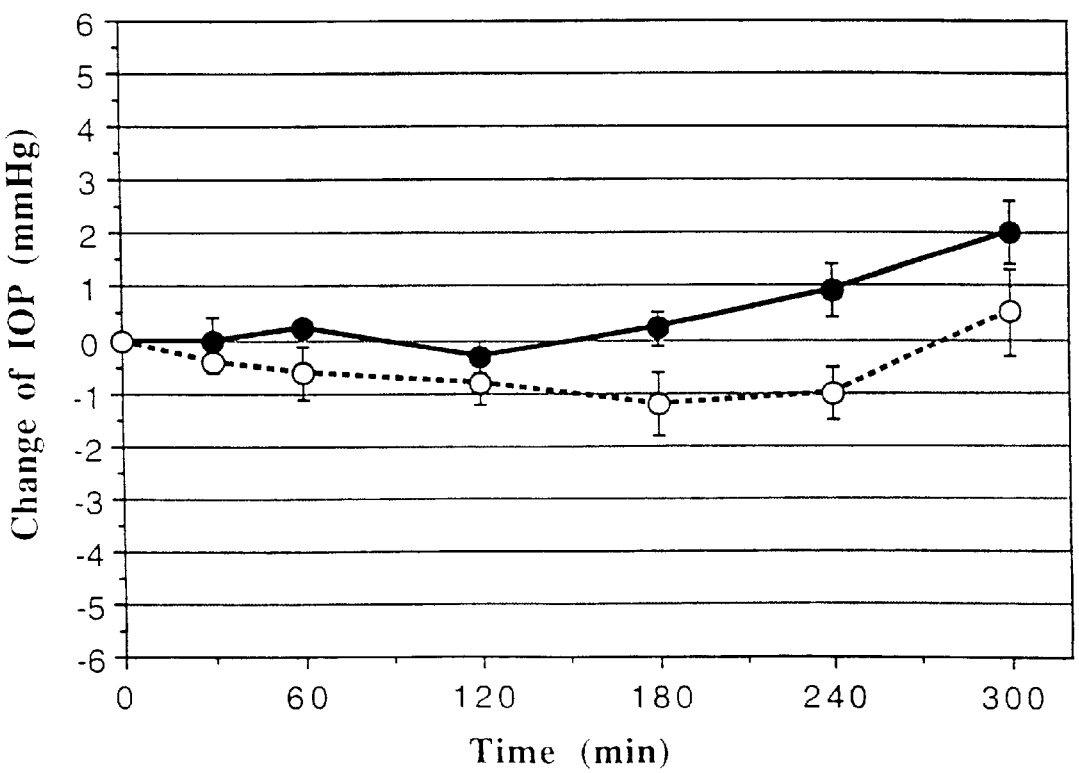
FIG. 12B shows the IOP changes in normotensive pigmented rabbits (untreated eyes) after unilateral ocular administration (25 μl) of 0.20% (w/v) arachidonyl N,N-dimethylaminoethylamide (○) or 0.9% (w/v) NaCl (•), mean±S.E. (n=6).

The results are shown in FIGS. 12A and 12B, and Table IV above. All of the values are expressed as mean±standard error of means (X±S.E.).

As shown in FIG. 12A and Table IV above, unilateral ocular administration of arachidonyl N,N-dimethylaminoethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl N,N-dimethylaminoethylamide showed a maximal IOP reduction of 0.8 mmHg, 4 hr after 0.2% (w/v) arachidonyl N,N-dimethylaminoethylamide treatment.

However, as shown in FIG. 12B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.2 mmHg, 3 hr after 0.2% (w/v) arachidonyl N,N-dimethylaminoethylamide treatment.

EXAMPLE 5

In this example, the effect of a 0.25% (w/v) arachidonyl N-acetylaminoethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl N-acetylaminoethylamide and 500 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 303 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 21.0–26.2 mmHg (n=6).

Figure 13A:
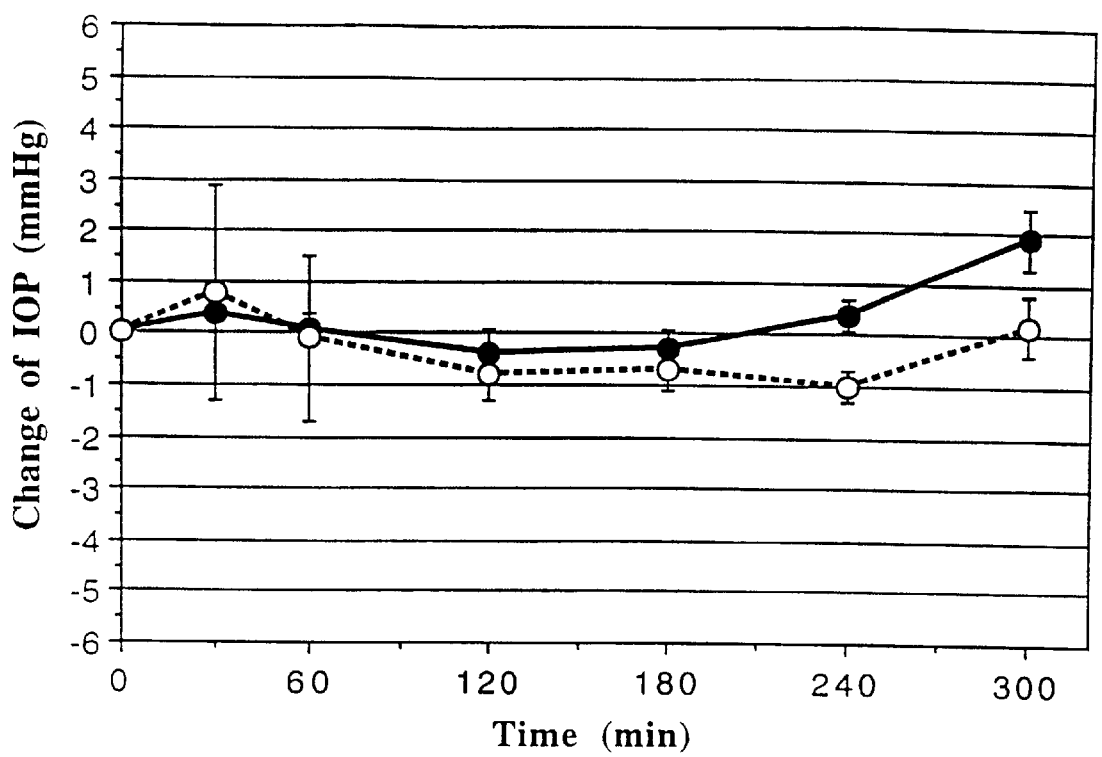
FIG. 13A shows the IOP changes in normotensive pigmented rabbits (treated eyes) after unilateral ocular administration (25 μl) of 0.25% (w/v) arachidonyl N-acetylaminoethylamide (○) or 0.9% (w/v) NaCl (•), mean±S.E. (n=6).
Figure 13B:
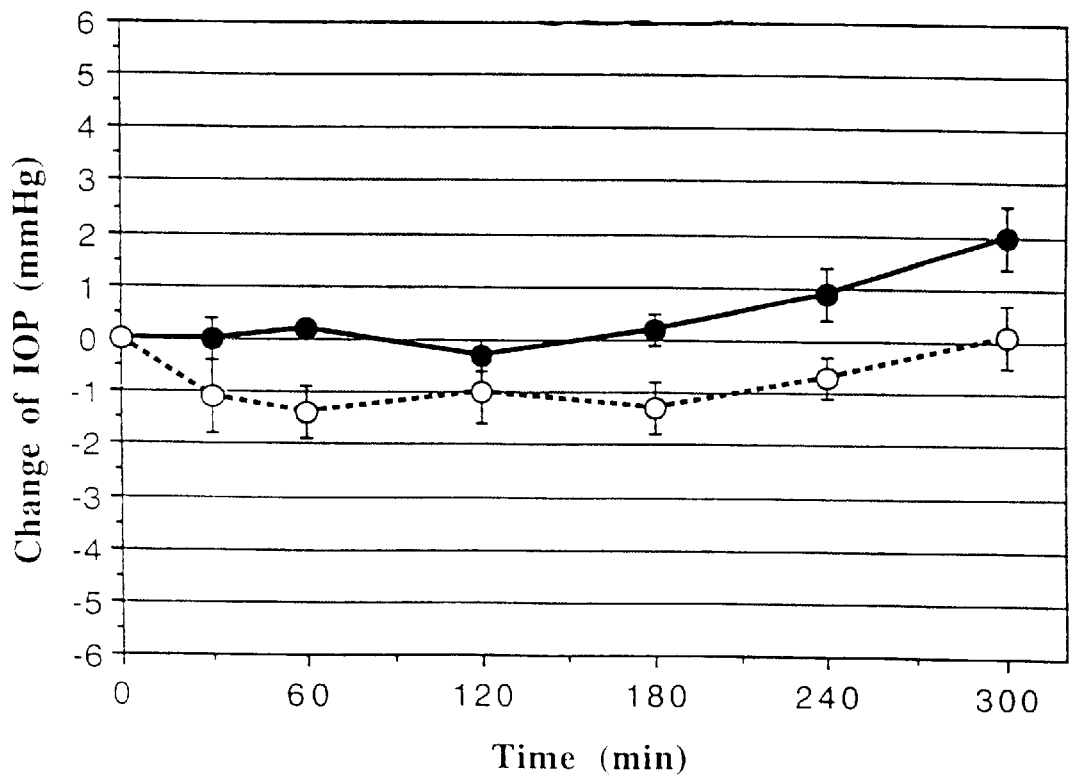
FIG. 13B shows the IOP changes in normotensive pigmented rabbits (untreated eyes) after unilateral ocular administration (25 μl) of 0.25% (w/v) arachidonyl N-acetylaminoethylamide (○) or 0.9% (w/v) NaCl (•), mean±S.E. (n=6).

The results are shown in FIGS. 13A and 13B, and Table IV above. All of the values are expressed as mean±standard error of means (X±S.E.).

As shown in FIG. 13A and Table IV above, unilateral ocular administration of arachidonyl N-acetylaminoethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl N-acetylaminoethylamide showed a maximal IOP reduction of 1.0 mmHg, 4 hr after 0.25% (w/v) arachidonyl N-acetylaminoethylamide treatment.

However, as shown in FIG. 13B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.4 mmHg, 1 hr after 0.25% (w/v) arachidonyl N-acetylaminoethylamide treatment.

EXAMPLE 6

In this example, the effect of a 0.25% (w/v) arachidonyl pyridinoethylamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl pyridinoethylamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 315 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 21.5–30.2 mmHg (n=6).

Figure 14A:
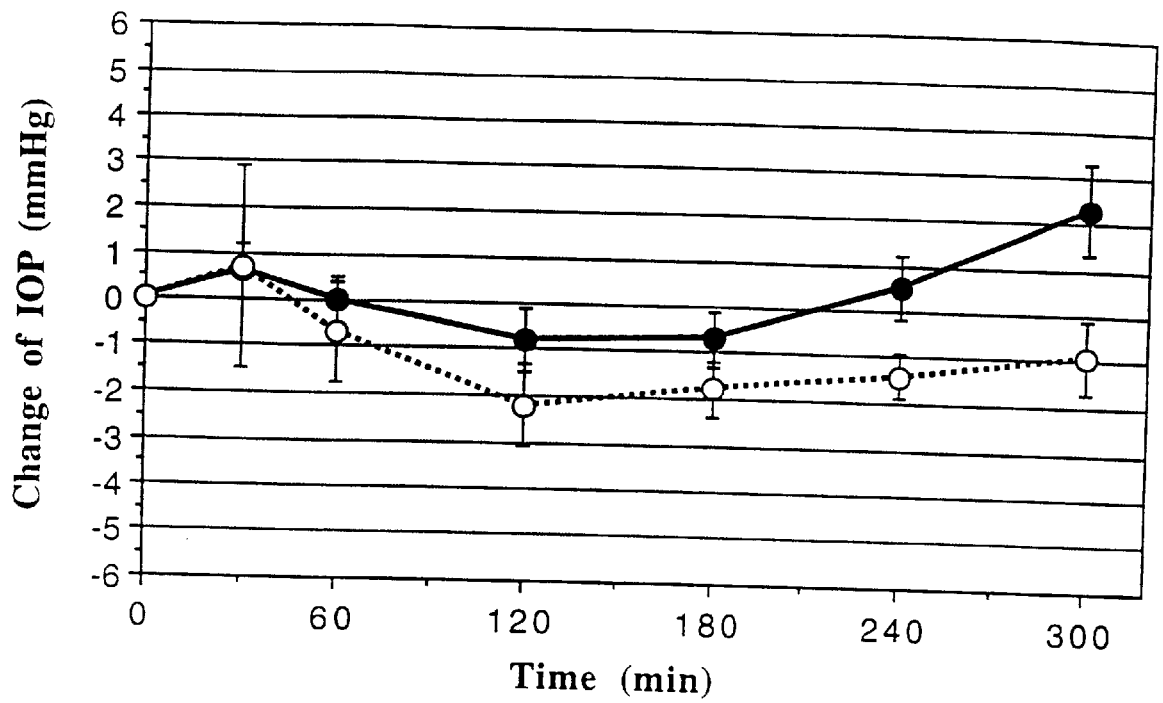
FIG. 14A shows the IOP changes in normotensive pigmented rabbits (treated eyes) after unilateral ocular administration (25 μl) of 0.25% (w/v) arachidonyl pyridinoethylamide (○) or 0.9% (w/v) NaCl (•), mean±S.E. (n=6).
Figure 14B:
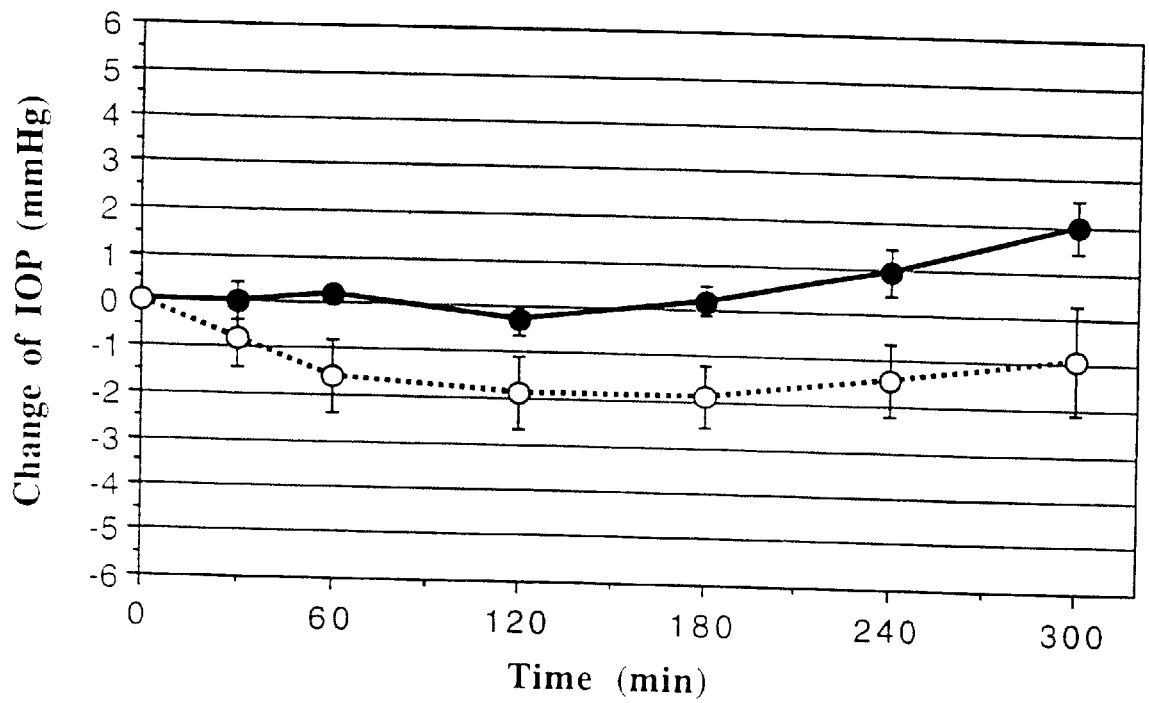
FIG. 14B shows the IOP changes in normotensive pigmented rabbits (untreated eyes) after unilateral ocular administration (25 μl) of 0.25% (w/v) arachidonyl pyridinoethylamide (○) or 0.9% (w/v) NaCl (•), mean±S.E. (n=6).

The results are shown in FIGS. 14A and 14B, and Table IV above. All of the values are expressed as mean±standard error of means (X±S.E.).

As shown in FIG. 14A and Table IV above, unilateral ocular administration of arachidonyl pyridinoethylamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl pyridinoethylamide showed a maximal IOP reduction of 2.2 mmHg, 2 hr after 0.25% (w/v) arachidonyl pyridinoethylamide treatment.

However, as shown in FIG. 14B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.9 mmHg, 2–3 hr after 0.25% (w/v) arachidonyl pyridinoethylamide treatment.

EXAMPLE 7

In this example, the effect of a 0.25% (w/v) arachidonyl propionitrileamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl propionitrileamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 302 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The JOPs of the pigmented rabbits at the time of eyedrop administration were between 23.0–30.4 mmHg (n=6).

Figure 15A:
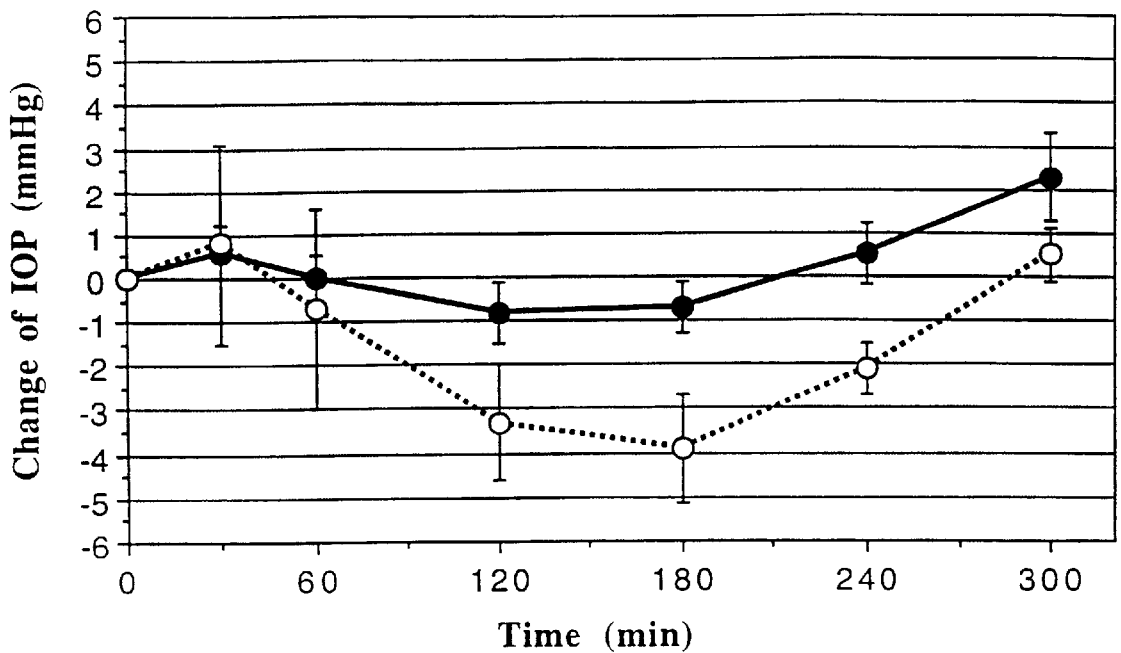
FIG. 15A shows the IOP changes in normotensive pigmented rabbits (treated eyes) after unilateral ocular administration (25 μl) of 0.25% (w/v) arachidonyl propionitrileamide (○) or 0.9% (w/v) NaCl (•), mean±S.E. (n=6).
Figure 15B:
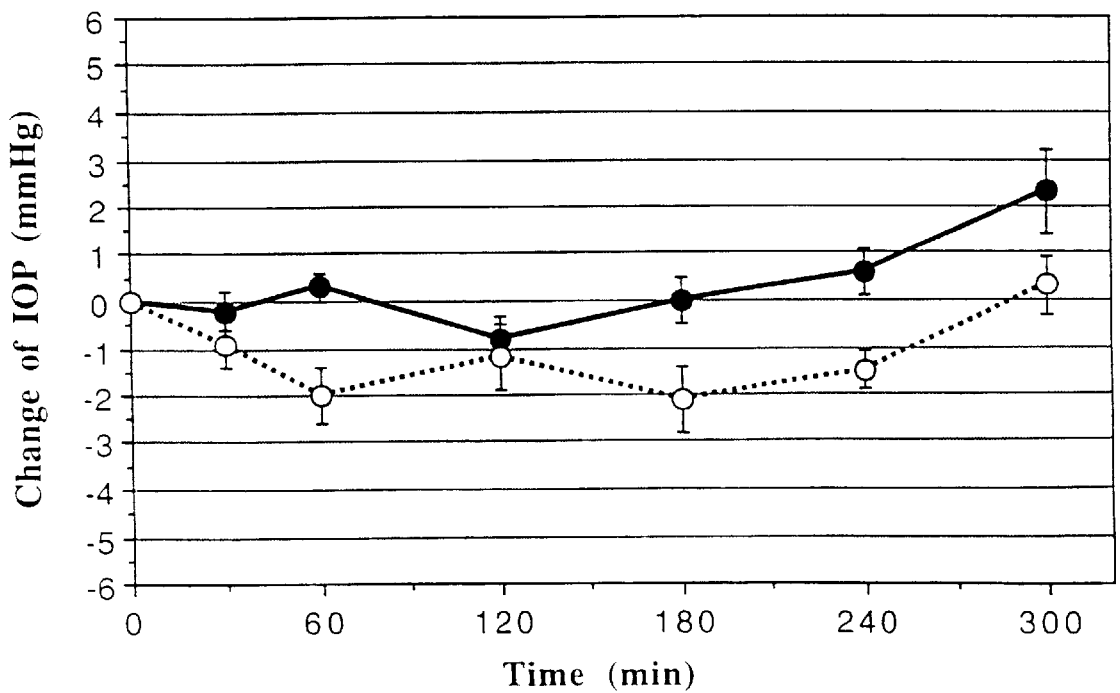
FIG. 15B shows the IOP changes in normotensive pigmented rabbits (untreated eyes) after unilateral ocular administration (25 μl) of 0.25% (w/v) arachidonyl propionitrileamide (○) or 0.9% (w/v) NaCl (•), mean±S.E. (n=6).

The results are shown in FIGS. 15A and 15B, and Table IV above. All of the values are expressed as mean±standard error of means (X±S.E.).

As shown in FIG. 15A and Table IV above, unilateral ocular administration of arachidonyl propionitrileamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl propionitrileamide showed a maximal IOP reduction of 3.9 mmHg, 3 hr after 0.25% (w/v) arachidonyl propionitrileamide treatment.

However, as shown in FIG. 15B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 2.0 mmHg, 1 hr after 0.25% (w/v) arachidonyl propionitrileamide treatment.

EXAMPLE 8

In this example, the effect of a 0.25% (w/v) arachidonyl morpholineamide solution on IOP of normotensive pigmented rabbits weighing between 30 2.6–3.6 kg (n=6) was studied. The rabbits were housed separately in cages under standard laboratory conditions, i.e., 10 hr dark/14 hr light cycle.

More specifically, 12.5 mg of arachidonyl morpholineamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 315 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 21.3–25.5 mmHg (n=6).

Figure 16A:
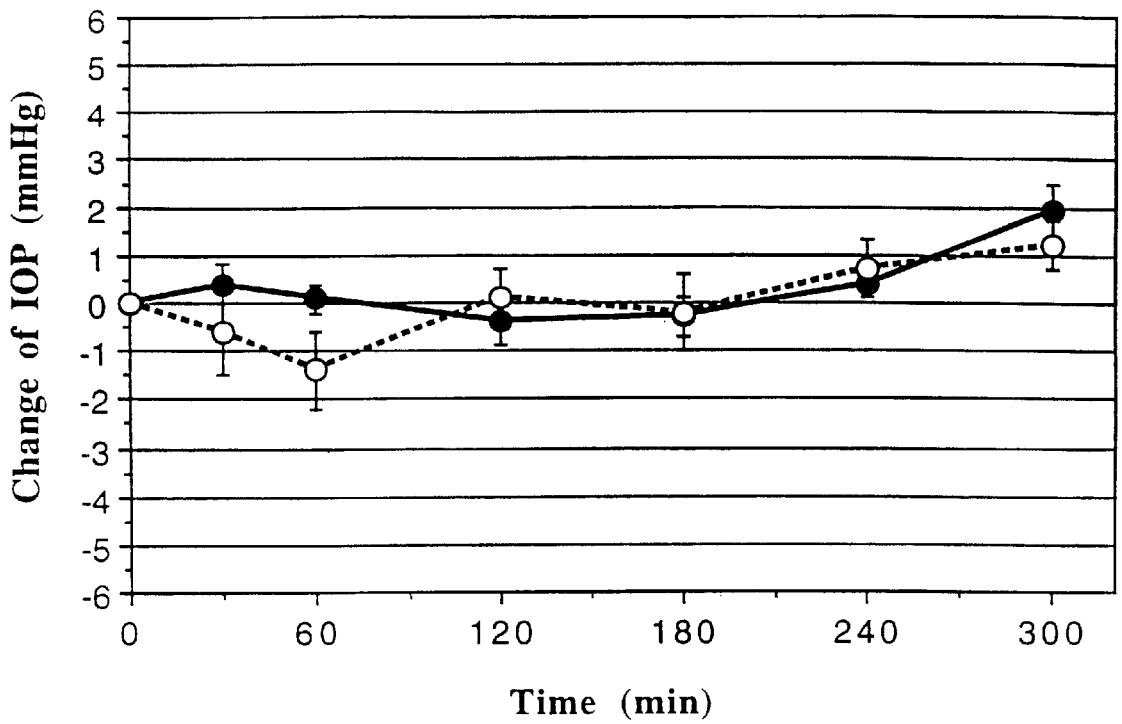
FIG. 16A shows the IOP changes in normotensive pigmented rabbits (treated eyes) after unilateral ocular administration (25 μl) of 0.25% (w/v) arachidonyl morpholineamide (○) or 0.9% (w/v) NaCl (•), mean±S.E. (n=6).
Figure 16B:
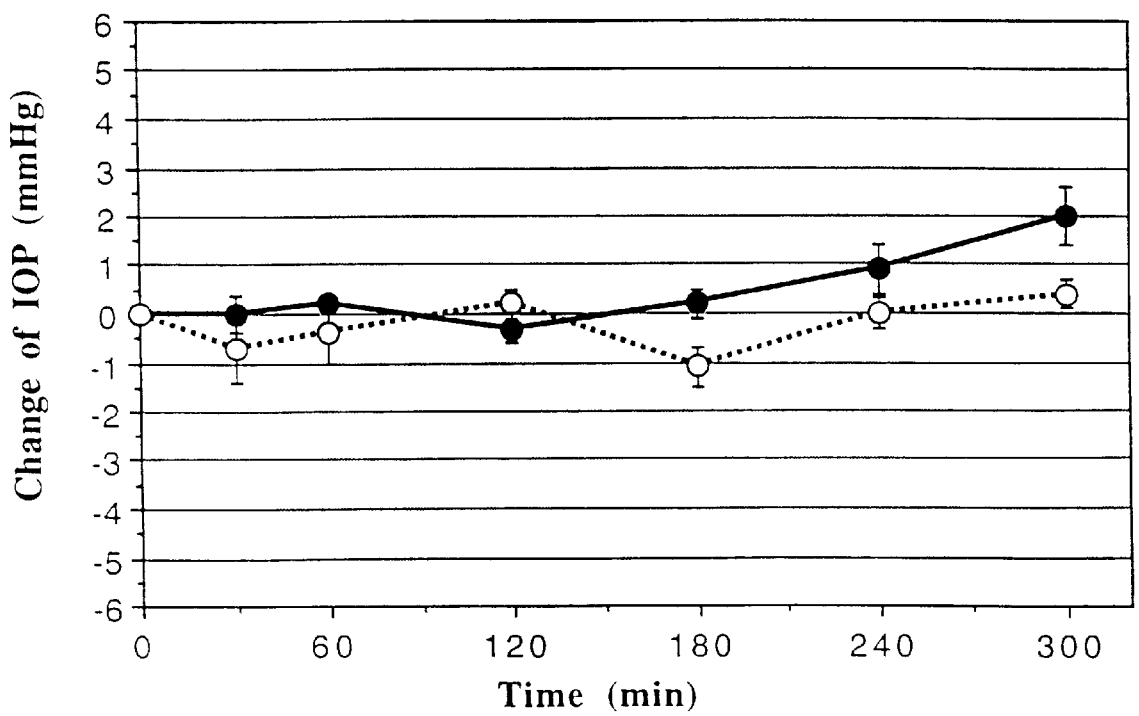
FIG. 16B shows the IOP changes in normotensive pigmented rabbits (untreated eyes) after unilateral ocular administration (25 μl) of 0.25% (w/v) arachidonyl morpholineamide (○) or 0.9% (w/v) NaCl (•), mean±S.E. (n=6).

The results are shown in FIGS. 16A and 16B, and Table IV above. All of the values are expressed as mean±standard error of means (X±S.E.).

As shown in FIG. 16A and Table IV above, unilateral ocular administration of arachidonyl morpholineamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl morpholineamide showed a maximal IOP reduction of 1.4 mmHg, 2 hr after 0.25% (w/v) arachidonyl morpholineamide treatment.

However, as shown in FIG. 16B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.1 mmHg, 2 hr after 0.25% (w/v) arachidonyl morpholineamide treatment.

Examples 9 to 11 below demonstrate that certain modifications of the carbon a to the amide nitrogen, according to Formula (II), eliminate the characteristic hypertensive phase seen by anandamides with alkylamide groups terminated by moieties which are not within the scope of Formula (I).

EXAMPLE 9

In this example, the effect of a 0.25% (w/v) arachidonyl α-dimethylethanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl α-dimethylethanolamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 321 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 19.6–28.9 mmHg (n=6).

Figure 17A:
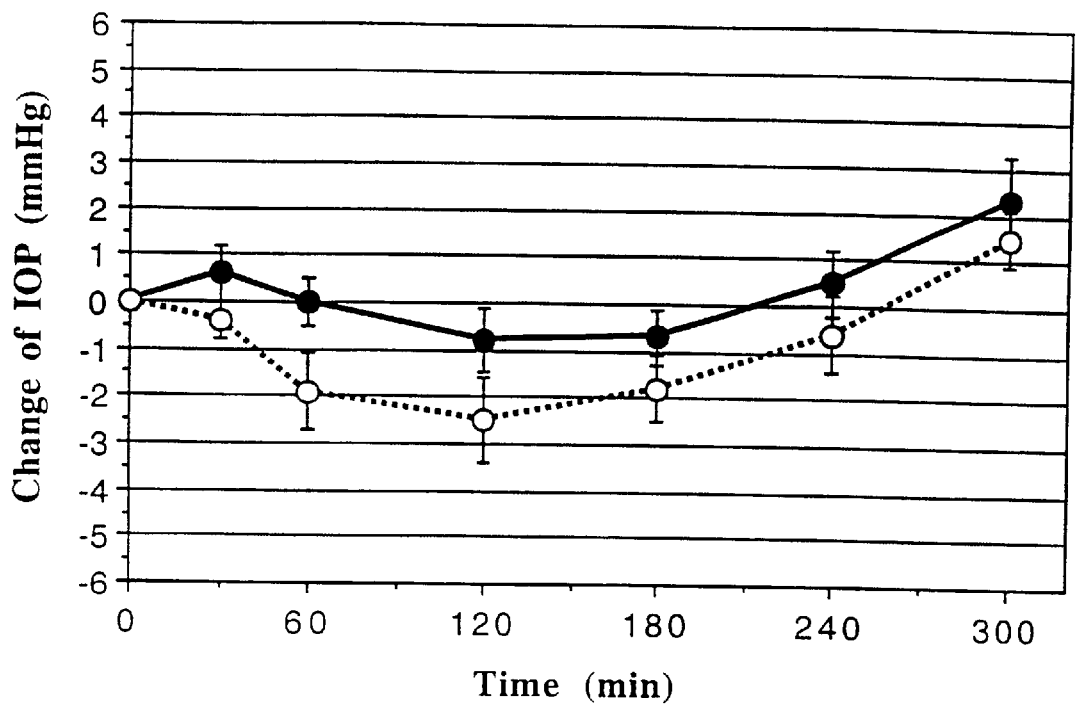
FIG. 17A shows the IOP changes in normotensive pigmented rabbits (treated eyes) after unilateral ocular administration (25 μl) of 0.25% (w/v) arachidonyl α-dimethylethanolamide (○) or 0.9% (w/v) NaCl (•), mean±S.E. (n=6).
Figure 17B:
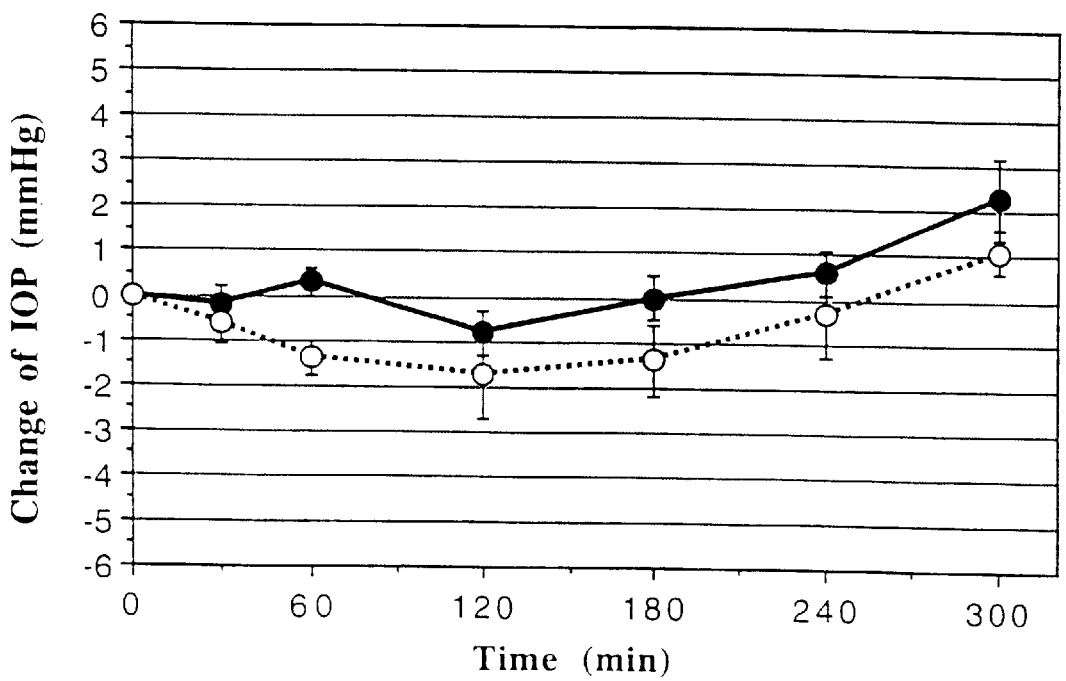
FIG. 17B shows the IOP changes in normotensive pigmented rabbits (untreated eyes) after unilateral ocular administration (25 μl) of 0.25% (w/v) arachidonyl α-dimethylethanolamide (○) or 0.9% (w/v) NaCl (•), mean±S.E. (n=6).

The results are shown in FIGS. 17A and 17B, and Table IV below. All of the values are expressed as mean±standard error of means (X±S.E.).

As shown in FIG. 17A and Table IV above, unilateral ocular administration of arachidonyl α-dimethylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl α-dimethylethanolamide showed a maximal IOP reduction of 2.5 mmHg, 2 hr after 0.25% (w/v) arachidonyl α-dimethylethanolamide treatment.

However, as shown in FIG. 17B and Table IV above, unilateral ocular administration does affect also on IOP in the contralateral (untreated) eye in normotensive pigmented rabbits when compared to administration of the 0.9% (w/v) NaCl solution. In the contralateral eye of normotensive pigmented rabbits, the maximal IOP reduction was 1.7 mmHg, 2 hr after 0.25% (w/v) arachidonyl α-dimethylethanolamide treatment.

EXAMPLE 10

In this example, the effect of a 0.25% (w/v) arachidonyl α-isopropylethanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 12.5 mg of arachidonyl α-isopropylethanolamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 308 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The JOPs of the pigmented rabbits at the time of eyedrop administration were between 21.4–29.5 mmHg (n=6).

Figure 18A:
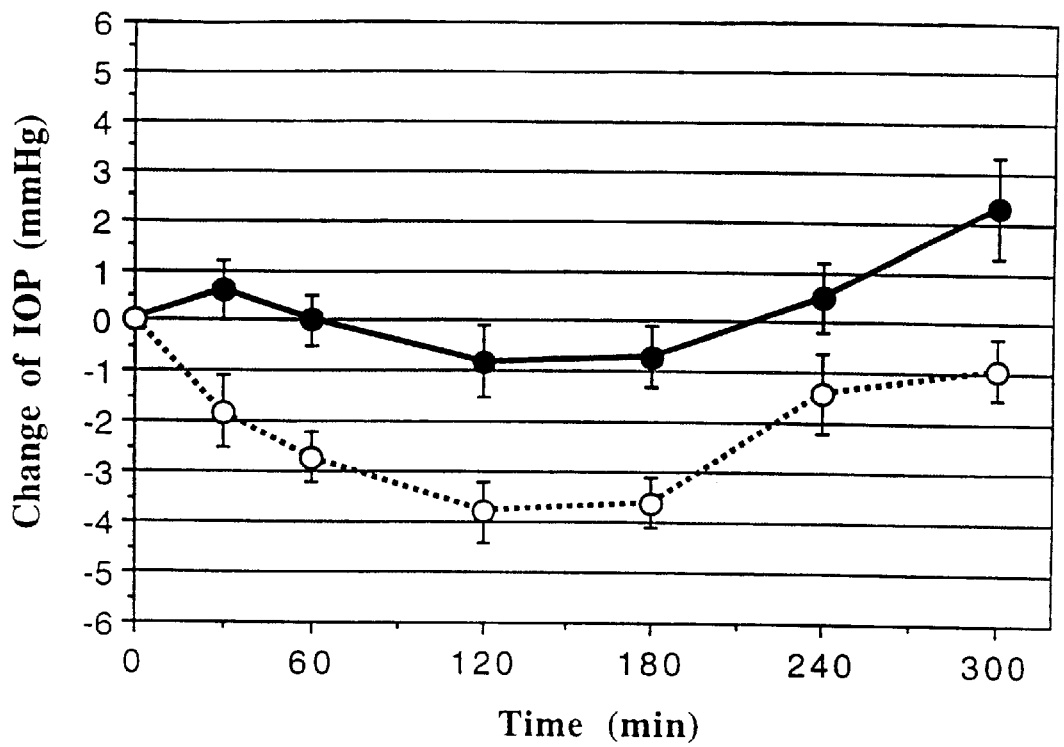
FIG. 18A shows the IOP changes in normotensive pigmented rabbits (treated eyes) after unilateral ocular administration (25 μl) of 0.25% (w/v) arachidonyl α-isopropylethanolamide (○) or 0.9% (w/v) NaCl (•), mean±S.E. (n=6).
Figure 18B:
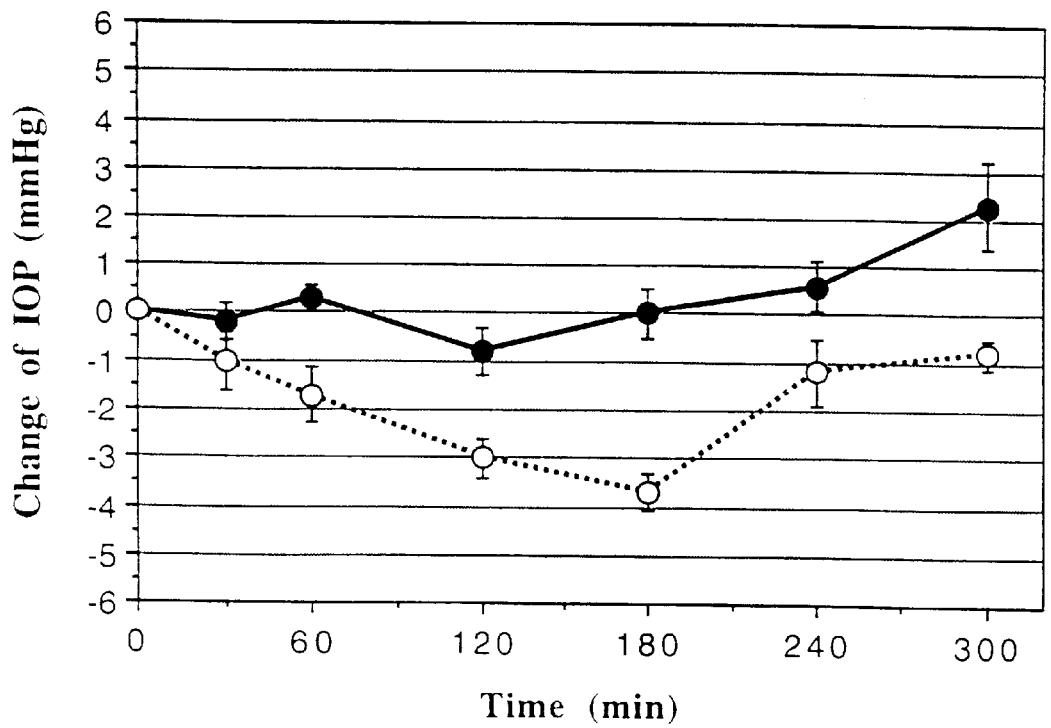
FIG. 18B shows the IOP changes in normotensive pigmented rabbits (untreated eyes) after unilateral ocular administration (25 μl) of 0.25% (w/v) arachidonyl α-isopropylethanolamide (○) or 0.9% (w/v) NaCl (•), mean±S.E. (n=6).

The results are shown in FIGS. 18A and 18B, and Table IV above. All of the values are expressed as mean±standard error of means (X±S.E.).

As shown in FIG. 18A and Table IV above, unilateral ocular administration of arachidonyl α-isopropylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl α-isopropylethanolamide showed a maximal IOP reduction of 3.8 mmHg, 2 hr after 0.25% (w/v) arachidonyl α-isopropylethanolamide treatment.

However, as shown in FIG. 18B and Table IV above, unilateral ocular administration does affect also on IOP in the contralateral (untreated) eye in normotensive pigmented rabbits when compared to administration of the 0.9% (w/v) NaCl solution. In the contralateral eye of normotensive pigmented rabbits, the maximal IOP reduction was 3.7 mmHg, 2 hr after 0.25% (w/v) arachidonyl α-isopropylethanolamide treatment.

EXAMPLE 11

In this example, the effect of a 0.20% (w/v) arachidonyl α-phenylethanolamide solution on IOP of normotensive pigmented rabbits weighing between 2.6–3.6 kg (n=6) was studied. The rabbits were housed separately in cages under standard laboratory conditions, i.e., 10 hr dark/14 hr light cycle.

More specifically, 10 mg of arachidonyl α-phenylethanolamide and 1000 mg of 2-OH-propyl-β-CD were added to distilled water, and the solution was adjusted to pH 7.0 with sodium hydroxide/hydrochloric acid. Then, distilled water was added to adjust the total volume to 5.0 ml. The osmolality of the solution was adjusted to isotonic, 319 mOsm/kg, with sodium chloride.

As a control, a 0.9% (w/v) NaCl was also prepared.

Then, 25 μl of either the drug-CD solution or the NaCl solution was administered unilaterally to the rabbits. The rabbits were kept in restraint boxes during the study.

IOP was measured using a BioRad (Cambridge, Mass.) Digilab Modular One Pneumatonometer. Before each measurement, one or two drops of 0.06% (w/v) oxybuprocaine were applied to the cornea as an anaesthetic before tonometry to eliminate discomfort. For each determination, at least two readings were taken from each eye. The measurements were started 2 hr before drug-CD or 0.9% (w/v) NaCl solution administration, and were continued for 5 hr after administration.

The IOPs of the pigmented rabbits at the time of eyedrop administration were between 19.2–29.6 mmHg (n=6).

Figure 19A:
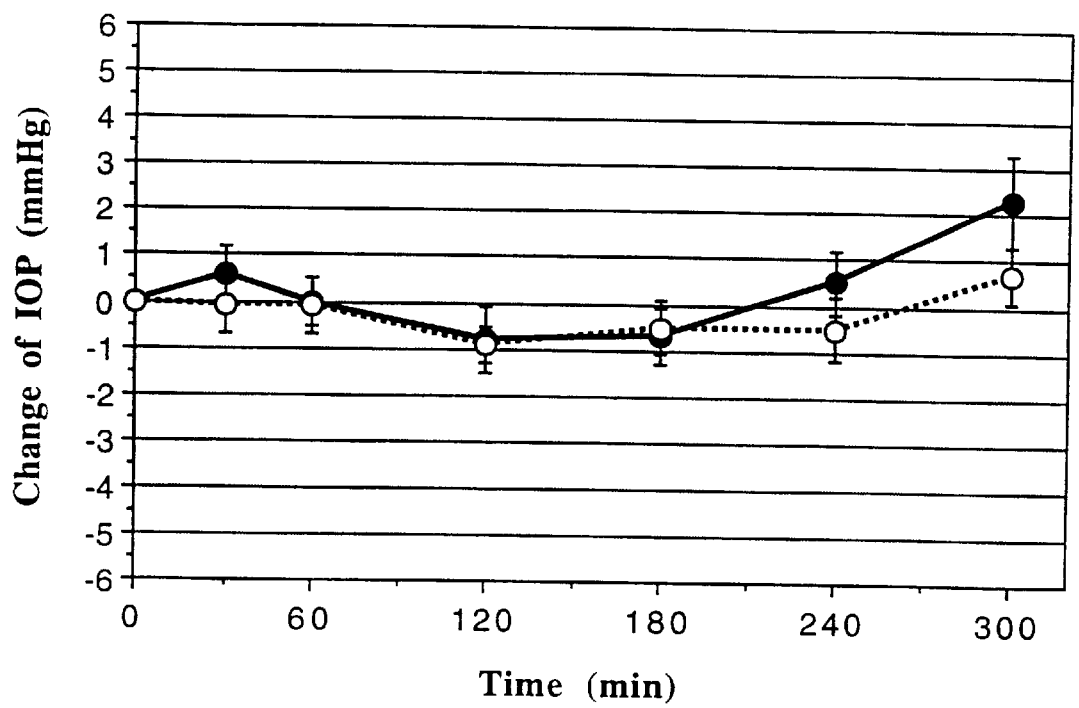
FIG. 19A shows the IOP changes in normotensive pigmented rabbits (treated eyes) after unilateral ocular administration (25 μl) of 0.20% (w/v) arachidonyl α-phenylethanolamide (○) or 0.9% (w/v) NaCl (•), mean±S.E. (n=6).
Figure 19B:
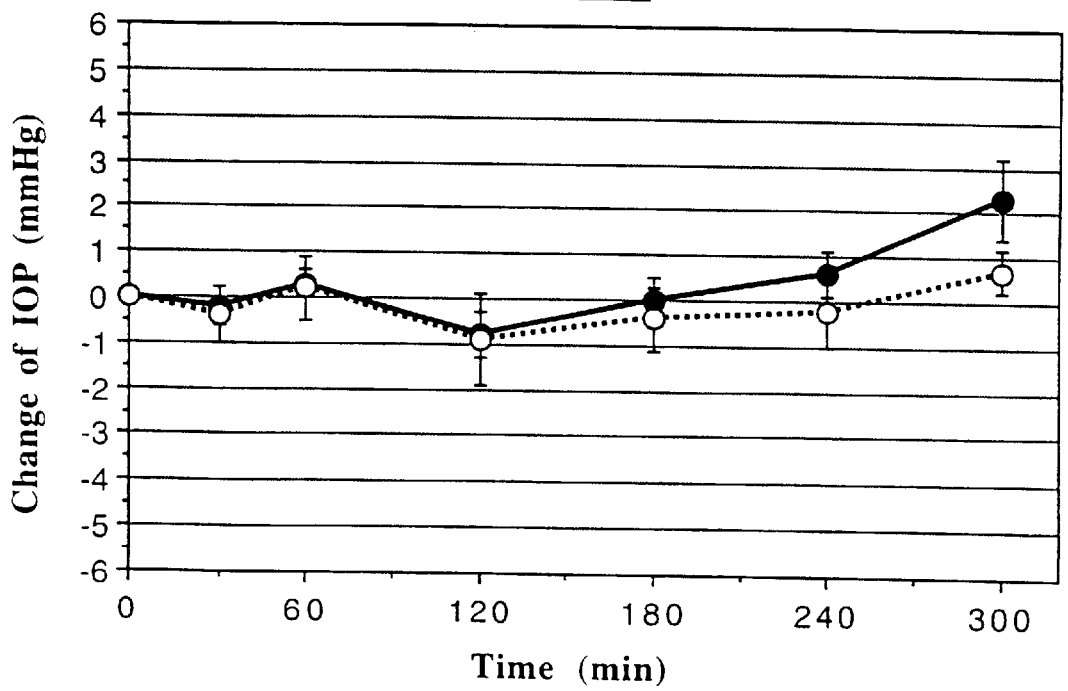
FIG. 19B shows the IOP changes in normotensive pigmented rabbits (untreated eyes) after unilateral ocular administration (25 μl) of 0.20% (w/v) arachidonyl α-phenylethanolamide (○) or 0.9% (w/v) NaCl (•), mean±S.E. (n=6).

The results are shown in FIGS. 19A and 19B, and Table IV above. All of the values are expressed as mean±standard error of means (X±S.E.).

As shown in FIG. 19A and Table IV above, unilateral ocular administration of arachidonyl α-phenylethanolamide decreases the IOP in treated eyes in normotensive pigmented rabbits when compared to administration of a 0.9% (w/v) NaCl solution. In the treated eyes of normotensive pigmented rabbits, cyclodextrin vehiculated arachidonyl α-phenylethanolamide showed a maximal IOP reduction of 0.9 mmHg, 2 hr after 0.2% (w/v) arachidonyl α-phenylethanolamide treatment.

However, as shown in FIG. 19B and Table IV above, unilateral ocular administration does affect also the IOP in the contralateral (untreated) eye in normotensive pigmented rabbits when compared to administration of the 0.9% (w/v) NaCl solution. In the contralateral eye of normotensive pigmented rabbits, the maximal IOP reduction was 0.9 mmHg, 2 hr after 0.2% (w/v) arachidonyl α-phenylethanolamide treatment.

Accordingly, based on the foregoing results, it is apparent that anandamides (or metabolites thereof) represented by Formula (I), such as ethanethiolamide, arachidonyl β-phenethylamide, arachidonyl aminoethylamide, arachidonyl N,N-dimethylaminoethylamide, arachidonyl N-acetylaminoethylamide, arachidonyl pyridinoethylamide, arachidonyl propionitrileamide, and arachidonyl morpholineamide appear to act to lower IOP without causing an appreciable initial hypertensive phase.

Also, based on the foregoing results, it is apparent that anandamides (or metabolites thereof) which act to lower IOP, but demonstrate an initial hypertensive phase, can be modified with a moiety at the carbon a to the amide nitrogen, to eliminate this effect, as represented by the anandamides of Formula (II). Examples of such a modification to eliminate this initial hypertensive phase include, but are not limited to, arachidonyl α-dimethylethanolamide, arachidonyl α-isopropylethanolamide, and arachidonyl α-phenylethanolamide.

These drugs appear to act locally within the treated eye, perhaps via a specific receptor or prostaglandin-mediated mechanism, rather than via the central nervous system. In cases where a contralateral eye IOP lowering effect occurs, uptake of the drug (or metabolites) diffused into the bloodstream from the treated eye is the probable mechanism of action (Salminen et al, *Exp. Eye Res.*, 38:203 (1984)). Although the mechanism of action by which anandamides represented by Formula (I) and Formula (II) produce their hypotensive effect in the eye is not entirely understood, these results indicate that they are promising drugs for treatment of intraocular hypertension. The results also indicate that cyclodextrin-vehiculated anandamides of Formula (I) and Formula (II) are suitable for topical ocular administration.

While the invention has been described in detail, and with reference to specific embodiments thereof, it will be apparent to one of ordinary skill in the art that various changes and modifications can be made therein without departing from the spirit and scope thereof.

What is claimed is:

1. An ophthalmic composition for reducing intraocular pressure comprising an admixture of:

(A) a pharmaceutically effective amount of an anandamide represented by Formula (I) or Formula (II):

Formula (I):

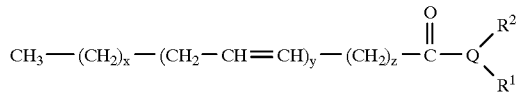

wherein
Q is N;
$R^1$ and $R^2$ are each H, an alkyl of from 1 to 3 carbon atoms or $(CH_2)_a$—$R^3$, wherein a is an integer of from 0 to 6;
$R^3$ is:
  (1) C≡N or SH;
  (2) a carbocyclic ring having from 3 to 7 carbon atoms or a heterocyclic ring having from 3 to 7 atoms, at least one of which is a heteroatom selected from the group consisting of N, O and S;
  (3) $R^4NR^5$, wherein $R^4$ and $R^5$ are each H or $(CH_2)_n$—$CR^6R^7R^8$, wherein n is an integer of from 0 to 3, and $R^6$, $R^7$ and $R^8$ are each H or $(CH_2)_p$—$CH_3$, wherein p is an integer of from 0 to 3; or
  (4)

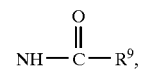

wherein $R^9$ is H or $(CH_2)_q CR^{10}R^{11}R^{12}$, wherein q is an integer of from 0 to 3, and $R^{10}$, $R^{11}$ and $R^{12}$ are each H or $(CH_2)_r$—$CH_3$, wherein r is an integer of from 0 to 3;
$R^1$ and $R^2$ may be combined together with Q to form a heterocyclic ring having 3 to 7 atoms, wherein the heterocyclic ring may have an additional heteroatom (s) selected from the group consisting of N, O and S, preferably morpholino;
x is an integer of from 0 to 18;
y is an integer of from 0 to 8; and
z is an integer of from 0 to 18;
wherein x+y+z≦36, or Formula (II):

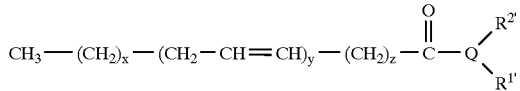

Q is N;
$R^{1'}$ and $R^{2'}$ are each H, an alkyl of from 1 to 3 carbon atoms or $(R^{4'}CR^{5'})$—$(CH_2)_a$—$R^{3'}$, wherein a' is an integer of from 0 to 5;
$R^{3'}$ is:
  (1) OH, SH, C≡CH, C≡N, F, Cl, Br or I;
  (2) a carbocyclic ring having from 3 to 7 carbon atoms, or a heterocyclic ring having from 3 to 7 atoms, at least one of which is a heteroatom selected from the group consisting of N, O and S;

(3) $R^4NR^5$, wherein $R^4$ and $R^5$ are each H or $(CH_2)_n$—$CR^6R^7R^8$, wherein n is an integer of from 0 to 3, and $R^6$, $R^7$ and $R^8$ are each H or $(CH_2)_p$—$CH_3$, wherein p is an integer of from 0 to 3;

(4)

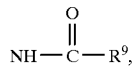

wherein $R^9$ is H or $(CH_2)_q$—$CR^{10}R^{11}R^{12}$, wherein q is an integer of from 0 to 3, and $R^{10}$, $R^{11}$ and $R^{12}$ are each H or $(CH_2)_r$—$CH_3$, wherein r is an integer of from 0 to 3; or (5) $OCR^{13}R^{14}R^{15}$, wherein $R^{13}$, $R^{14}$, $R^{15}$ are each H or $(CH_2)_s$—$CH_3$, wherein s is an integer of from 0 to 3;

$R^{4'}$ and $R^{5'}$ are each H, $(CH_2)_l$—$R^{3'}$, wherein $R^{3'}$ is a carbocyclic ring having from 3 to 7 carbon atoms, or a heterocyclic ring having from 3 to 7 atoms, at least one of which is a heteroatom selected from the group consisting of N, O and S, or $(CH_2)_l$—$CR^{6'}R^{7'}R^{8'}$, wherein l is an integer of from 0 to 3, and $R^{6'}$, $R^{7'}$, and $R^{8'}$ are each H or $(CH_2)_m$—$CH_3$, wherein m is an integer of from 0 to 3;

$R^{1'}$ and $R^{2'}$ may be combined together with Q to form a heterocyclic ring having 3 to 7 atoms, wherein the heterocyclic ring may have an additional heteroatom(s) selected from the group consisting of N, O and S;

$R^{4'}$ and $R^{5'}$ may be combined together to form a carbocyclic ring having from 3 to 7 carbon atoms, or may be combined with a heteroatom(s) selected from the group consisting of N, O and S to form a heterocyclic ring having from 3 to 7 atoms;

$R^4$ or $R^5$ may be combined together with Q to form a heterocyclic ring having from 3 to 7 atoms, wherein the heterocyclic ring may have an additional heteroatom(s) selected from the group consisting of N, O and S;

x is an integer of from 0 to 18;

y is an integer of from 0 to 8; and z is an integer of from 0 to 18;

wherein $x+y+z \leq 36$; and (B) a cyclodextrin.

2. The ophthalmic composition according to claim 1, wherein a is an integer of from 1 to 4, a' is an integer of 0 to 3.

3. The ophthalmic composition according to claim 2, wherein a is an integer of from 2 to 3.

4. The ophthalmic composition according to claim 1, wherein one of $R_1$ and $R^2$ is H or an alkyl having from 1 to 3 carbon atoms and the other of $R^1$ and $R^2$ is $(CH_2)_a$—$R^3$; and one of $R^{1'}$ and $R^{2'}$ is H or an alkyl having from 1 to 3 carbon atoms and the other of $R^{1'}$ and $R^{2'}$ is $(R^{4'}CR^{5'})$—$(CH_2)_{a'}$—$R^{3'}$.

5. The ophthalmic composition according to claim 1, wherein

Q is N;

$R^3$ is:
(1) $C \equiv N$;
(2) the carbocylic ring is phenyl, and the heterocyclic ring is pyridino or morpholino; or
(3) $R^4NR^5$, wherein $R^4$ and $R^5$ are each H or $(CH_2)_n$—$CR^6R^7R^8$, wherein n is an integer of from 0 to 1, and $R^6$, $R^7$ and $R^8$ are each H or $(CH_2)_p$—$CH_3$, wherein p is an integer of from 0 to 1; or (4)

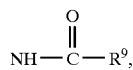

wherein $R^9$ is H or $(CH_2)_q$—$CR^{10}R^{11}R^{12}$, wherein q is an integer of from 0 to 1, and $R^{10}$, $R^{11}$ and $R^{12}$ are each H or $(CH_2)_r$—$CH_3$, wherein r is an integer of from 0 to 3;

$R^{3'}$ is:
(1) SH, F, $C \equiv CH$ or $C \equiv N$;
(2) the carbocylic ring is phenyl, and the heterocyclic ring is pyridino or morpholino;
(3) $R^4NR^5$, wherein $R^4$ and $R^5$ are each H or $(CH_2)_n$—$CR^6R^7R^8$, wherein n is an integer of from 0 to 1, and $R^6$, $R^7$ and $R^8$ are each H or $(CH_2)_p$—$CH_3$, wherein p is an integer of from 0 to 1;

(4)

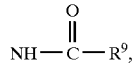

wherein $R^9$ is H or $(CH_2)_q$—$CR^{10}R^{11}R^{12}$, wherein q is an integer of from 0 to 1, and $R^{10}$, $R^{11}$ and $R^{12}$ are each H or $(CH_2)_r$—$CH_3$, wherein r is an integer of from 0 to 3; or (5) $OCR^{13}R^{14}R^{15}$, wherein $R^{13}$, $R^{14}$, $R^{15}$ are each H or $(CH_2)_s$—$CH_3$, wherein s is an integer of from 0 to 1;

l is 0 to 1; only one of $R^{4'}$ and $R^{5'}$ is H;

$R^1$ and $R^2$ may be combined together with Q to form a morpholino; and $R^{1'}$ and $R^{2'}$ may be combined together with Q to form a morpholino; and x is an integer of from 2 to 5;

y is an integer of from 2 to 4; and z is an integer of from 2 to 5 wherein $x+y+z \leq 24$.

6. The ophthalmic composition according to claim 5, wherein $R^3$ is $C \equiv N$, and $R^{3'}$ is $C \equiv CH$ or $C \equiv N$.

7. The ophthalmic composition according to claim 6, wherein $R^{3'}$ is $C \equiv N$.

8. The ophthalmic composition according to claim 1, wherein said anandamide is selected from the group consisting of arachidonyl ethanethiolamide, arachidonyl β-phenethylamide, arachidonyl aminoethylamide, arachidonyl N,N-dimethylaminoethylamide, arachidonyl N-acetylaminoethylamide, arachidonyl pyridinoethylamide, arachidonyl propionitrileamide, arachidonyl morpholineamide, arachidonyl α-isopropylethanolamide, arachidonyl α-methylethanolamide, arachidonyl α-dimethylethanolamide, arachidonyl α-phenylethanolamide, arachidonyl α-isobutylethanolamide, and arachidonyl α-tert-butylethanolamide.

9. The ophthalmic composition according to claim 1, wherein said cyclodextrin is 2-hydroxypropyl-β-cyclodextrin or heptakis-(2,6-O-methyl)-β-cyclodextrin.

10. The ophthalmic composition according to claim 1, wherein said ophthalmic composition is an aqueous solution containing 0.01 to 2.0% (w/v) of said anandamide represented by Formula (I) or (II), and 0.5 to 40% (w/v) of a cyclodextrin.

11. The ophthalmic composition according to claim 10, wherein said ophthalmic composition is an aqueous solution containing 0.1 to 0.5% (w/v) of said anandamide represented by Formula (I) or (II), and 5.0 to 25% (w/v) of a cyclodextrin.

12. The ophthalmic composition according to claim 10, wherein the composition further comprises a water-soluble polymeric compound as a viscosity enhancing agent.

13. The ophthalmic composition according to claim 12, wherein said water-soluble polymeric compound is selected from the group consisting of hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid, and polyacrylic acid.

14. The ophthalmic composition according to claim 12, wherein the viscosity enhancing agent is present in an amount to give a viscosity in the range of 1 to 1,000 cP.

15. The ophthalmic composition according to claim 14, wherein the viscosity enhancing agent is present in an amount to give a viscosity in the range of 5 to 50 cP.

16. The ophthalmic composition according to claim 10, wherein the composition further comprises a buffering agent.

17. The ophthalmic composition according to claim 16, wherein said buffering agent is selected from the group consisting of acetate, citrate, phosphate, borate buffers, and a mixture thereof.

18. The ophthalmic composition according to claim 16, wherein the concentration of the buffering agent is about 1.0 mM to 200 mM.

19. The ophthalmic composition according to claim 18, wherein the concentration of the buffering agent is about 10 mM to 100 mM.

20. The ophthalmic composition according to claim 16, wherein the solution has a pH in the range of 4.0 to 8.0.

21. A method for the treatment of intraocular hypertension, comprising topically administering to an eye of a subject in need of such treatment, a pharmaceutically effective amount of an anandamide represented by Formula (I):

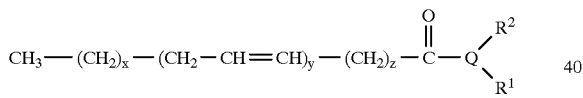

wherein
Q is N;
$R^1$ and $R^2$ are each H, an alkyl of from 1 to 3 carbon atoms or $(CH_2)_a$—$R^3$, wherein a is an integer of from 0 to 6;
$R^3$ is:
(1) C≡N or SH;
(2) a carbocyclic ring having from 3 to 7 carbon atoms, or a heterocyclic ring having from 3 to 7 atoms, at least one of which is a heteroatom selected from the group consisting of N, O and S;
(3) $R^4NR^5$, wherein $R^4$ and $R^5$ are each H or $(CH_2)_n$—$CR^6R^7R^8$, wherein n is an integer of from 0 to 3, and $R^6$, $R^7$ and $R^8$ are each H or $(CH_2)_p$—$CH_3$, wherein p is an integer of from 0 to 3; or
(4)

wherein $R^9$ is H or $(CH_2)_q$—$CR^{10}R^{11}R^{12}$, wherein q is an integer of from 0 to 3, and $R^{10}$, $R^{11}$ and $R^{12}$ are each H or $(CH_2)_r$—$CH_3$, wherein r is an integer of from 0 to 3;

$R^1$ and $R^2$ may be combined together with Q to form a heterocyclic ring having 3 to 7 atoms, wherein the heterocyclic ring may have an additional heteroatom(s) selected from the group consisting of N, O and S, preferably morpholino;
x is an integer of from 0 to 18;
y is an integer of from 0 to 8; and
z is an integer of from 0 to 18;
wherein x+y+z≦36, or Formula (II):

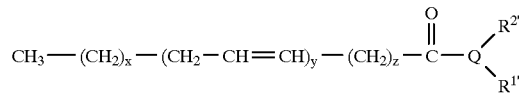

Q is N;
$R^{1'}$ and $R^{2'}$ are each H, an alkyl of from 1 to 3 carbon atoms or $(R^{4'}CR^{5'})$—$(CH_2)_{a'}$—$R^{3'}$, wherein a' is an integer of from 0 to 5;
$R^{3'}$ is:
(1) OH, SH, C≡CH, C≡N, F, Cl, Br or I;
(2) a carbocyclic ring having from 3 to 7 carbon atoms, or a heterocyclic ring having from 3 to 7 atoms, at least one of which is a heteroatom selected from the group consisting of N, O and S;
(3) $R^4NR^5$, wherein $R^4$ and $R^5$ are each H or $(CH_2)_n$—$CR^6R^7R^8$, wherein n is an integer of from 0 to 3, and $R^6$, $R^7$ and $R^8$ are each H or $(CH_2)_p$—$CH_3$, wherein p is an integer of from 0 to 3;
(4)

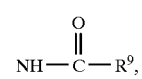

wherein $R^9$ is H or $(CH_2)_q$—$CR^{10}R^{11}R^{12}$, wherein q is an integer of from 0 to 3, and $R^{10}$, $R^{11}$ and $R^{12}$ are each H or $(CH_2)_r$—$CH_3$, wherein r is an integer of from 0 to 3; or
(5) $OCR^{13}R^{14}R^{15}$, wherein $R^{13}$, $R^{14}$, $R^{15}$ are each H or $(CH_2)_s$—$CH_3$, wherein s is an integer of from 0 to 3;

$R^{4'}$ and $R^{5'}$ are each H, $(CH_2)_l$—$R^{3'}$, wherein $R^{3'}$ is a carbocyclic ring having from 3 to 7 carbon atoms, or a heterocyclic ring having from 3 to 7 atoms, at least one of which is a heteroatom selected from the group consisting of N, O and S, or $(CH_2)_l$—$CR^{6'}R^{7'}R^{8'}$, wherein l is an integer of from 0 to 3, and $R^{6'}$, $R^{7'}$, and $R^{8'}$ are each H or $(CH_2)_m$—$CH_3$, wherein m is an integer of from 0 to 3;

$R^{1'}$ and $R^{2'}$ may be combined together with Q to form a heterocyclic ring having 3 to 7 atoms, wherein the heterocyclic ring may have an additional heteroatom(s) selected from the group consisting of N, O and S;

$R^{4'}$ and $R^{5'}$ may be combined together to form a carbocyclic ring having from 3 to 7 carbon atoms, or may be combined with a heteroatom(s) selected from the group consisting of N, O and S to form a heterocyclic ring having from 3 to 7 atoms;

$R^4$ or $R^5$ may be combined together with Q to form a heterocyclic ring having 3 to 7 atoms, wherein the heterocyclic ring may have an additional heteroatom(s) selected from the group consisting of N, O and S;

x is an integer of from 0 to 18;

y is an integer of from 0 to 8; and z is an integer of from 0 to 18;

wherein x+y+z≦36; and (B) a cyclodextrin.

22. The method according to claim 21, wherein a is an integer of from 1 to 4, a' is an integer of 0 to 3.

23. The method according to claim 22, wherein a is an integer of from 2 to 3.

24. The method according to claim 21, wherein one of $R^1$ and $R^2$ is H or an alkyl having from 1 to 3 carbon atoms and the other of $R^1$ and $R^2$ is $(CH_2)_a$—$R^3$; and one of $R^{1'}$ and $R^{2'}$ is H or an alkyl having from 1 to 3 carbon atoms and the other of $R^{1'}$ and $R^{2'}$ is $(R^{4'}CR^{5'})$—$(CH_2)_a$—$R^{3'}$.

25. The method according to claim 1, wherein

Q is N;

$R^3$ is:

(1) C≡N;

(2) the carbocylic ring is phenyl, and the heterocyclic ring is pyridino or morpholino; or (3) $R^4NR^5$, wherein $R^4$ and $R^5$ are each H or $(CH_2)_n$—$CR^6R^7R^8$, wherein n is an integer of from 0 to 1, and $R^6$, $R^7$ and $R^8$ are each H or $(CH_2)_p$—$CH_3$, wherein p is an integer of from 0 to 1; or (4)

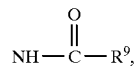

wherein $R^9$ is H or $(CH_2)_q$—$CR^{10}OR^{11}R^{12}$, wherein q is an integer of from 0 to 1, and $R^{10}$, $R^{11}$ and $R^{12}$ are each H or $(CH_2)_r$—$CH_3$, wherein r is an integer of from 0 to 3;

$R^{3'}$ is:

(1) SH, F, C≡CH or C≡N;

(2) the carbocylic ring is phenyl, and the heterocyclic ring is pyridino or morpholino;

(3) $R^4NR^5$, wherein $R^4$ and $R^5$ are each H or $(CH_2)_n$—$CR^6R^7R^8$, wherein n is an integer of from 0 to 1, and $R^6$, $R^7$ and $R^8$ are each H or $(CH_2)_p$—$CH_3$, wherein p is an integer of from 0 to 1;

(4)

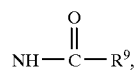

wherein $R^9$ is H or $(CH_2)_q$—$CR^{10}R^{11}R^{12}$, wherein q is an integer of from 0 to 1, and $R^{10}$, $R^{11}$ and $R^{12}$ are each H or $(CH_2)_r$—$CH_3$, wherein r is an integer of from 0 to 3; or (5) $OCR^{13}R^{14}R^{15}$, wherein $R^{13}$, $R^{14}$, $R^{15}$ are each H or $(CH_2)_s$—$CH_3$, wherein s is an integer of from 0 to 1;

l is 0 to 1; only one of $R^{4'}$ and $R^{5'}$ is H;

$R^1$ and $R^2$ may be combined together with Q to form a morpholino; and $R^{1'}$ and $R^{2'}$ may be combined together with Q to form a morpholino; and x is an integer of from 2 to 5;

y is an integer of from 2 to 4; and z is an integer of from 2 to 5 wherein x+y+z≦24.

26. The method according to claim 25, wherein $R^3$ is C≡N, and $R^{3'}$ is C≡CH or C≡N.

27. The method according to claim 21, wherein $R^{3'}$ is C≡N.

28. The method according to claim 21, wherein said anandamide is selected from the group consisting of arachidonyl ethanethiolamide, arachidonyl β-phenethylamide, arachidonyl aminoethylamide, arachidonyl N,N-dimethylaminoethylamide, arachidonyl N-acetylaminoethylamide, arachidonyl pyridinoethylamide, arachidonyl propionitrileamide, arachidonyl morpholineamide, arachidonyl α-isopropylethanolamide, arachidonyl α-methylethanolamide, arachidonyl α-dimethylethanolamide, arachidonyl α-phenylethanolamide, arachidonyl α-iso-butylethanolamide, and arachidonyl α-tert-butylethanolamide.

29. The method according to claim 21, wherein said anandamide is co-administered with a cyclodextrin.

30. The method according to claim 29, said cyclodextrin is 2-hydroxypropyl-β-cyclodextrin or heptakis-(2,6-O-methyl)-β-cyclodextrin.

31. The method according to claim 29, wherein said ophthalmic composition is an aqueous solution containing 0.01 to 2.0% (w/v) of said anandamide represented by Formula (I) or (II), and 0.5 to 40% (w/v) of a cyclodextrin.

32. The method according to claim 31, wherein said ophthalmic composition is an aqueous solution containing 0.1 to 0.5% (w/v) of said anandamide represented by Formula (I) or (II), and 5.0 to 25% (w/v) of a cyclodextrin.

33. The method according to claim 31, wherein the composition further comprises a water-soluble polymeric compound as a viscosity enhancing agent.

34. The method according to claim 33, wherein said water-soluble polymeric compound is selected from the group consisting of hydroxypropylmethyl cellulose, hydroxyethyl cellulose, hydroxypropyl cellulose, methyl cellulose, polyvinyl alcohols, sodium polyacrylate, sodium carboxymethyl cellulose, polyvinyl pyrrolidone, hyaluronic acid, and polyacrylic acid.

35. The method according to claim 33, wherein the viscosity enhancing agent is present in an amount to give a viscosity in the range of 1 to 1,000 cP.

36. The method according to claim 35, wherein the viscosity enhancing agent is present in an amount to give a viscosity in the range of 5 to 50 cP.

37. The method according to claim 31, wherein the composition further comprises a buffering agent.

38. The method according to claim 37, wherein said buffering agent is selected from the group consisting of acetate, citrate, phosphate, borate buffers, and a mixture thereof.

39. The method according to claim 37, wherein the concentration of the buffering agent is about 1.0 mM to 200 mM.

40. The method according to claim 39, wherein the concentration of the buffering agent is about 10 mM to 100 mM.

41. The method according to claim 37, wherein the solution has a pH in the range of 4.0 to 8.0.

* * * * *